United States Patent [19]
Canard et al.

[11] Patent Number: 5,798,210
[45] Date of Patent: Aug. 25, 1998

[54] DERIVATIVES UTILIZABLE IN NUCLEIC ACID SEQUENCING

[75] Inventors: Bruno Canard, Nice; Simon Sarfati, Paris, both of France

[73] Assignee: Institut Pasteur, Paris Cedex, France

[21] Appl. No.: 525,504

[22] PCT Filed: Mar. 28, 1994

[86] PCT No.: PCT/FR94/00345

§ 371 Date: Nov. 20, 1995

§ 102(e) Date: Nov. 20, 1995

[87] PCT Pub. No.: WO94/23064

PCT Pub. Date: Oct. 13, 1994

[30] Foreign Application Priority Data

Mar. 26, 1993 [FR] France .................. 93 03538

[51] Int. Cl.$^6$ .................................. C12Q 1/68
[52] U.S. Cl. ............ 435/6; 435/91.1; 436/501; 536/22.1; 536/23.1; 536/24.1; 536/24.3; 536/24.31; 536/24.32; 536/24.33; 536/25.3; 935/76; 935/77

[58] Field of Search ............ 435/6, 91.1; 436/501; 536/22.1, 23.1, 24.1, 24.3–24.33, 25.3; 935/77.76

[56] References Cited

PUBLICATIONS

Sarfati et al. (1991) Tetrahedron Letters, vol. 32, No. 36, pp. 4699–4702.

Woodward et al. (1991) Biochemisry, vol. 30, pp. 422–430.

*Primary Examiner*—Ardin H. Marschel
*Attorney, Agent, or Firm*—Oblon, Spivak, McClelland, Maier & Neustadt, P.C.

[57] ABSTRACT

Deoxyribonucleotide 5' triphosphate (dNTP) or ribonucleotide 5' triphosphate (NTP) esters for use in a nucleic acid sequencing process without use of a gel and having one o formulae (I), (II), (III) or (IV).

19 Claims, 13 Drawing Sheets

DERIVATIVES UTILIZABLE IN NUCLEIC ACID SEQUENCING

This application is a 371 filing of PCT/FR94/00345, filed Mar. 28, 1994.

The present invention relates to the synthesis of 2'-deoxy-ribonucleoside 5' triphosphates substituted at the 3' position of the deoxyribose corresponding to the four nucleotide bases A, T, C and G and their use in a novel sequencing method for nucleic acids.

The 3' position is esterified by a specific derivative conferring on each nucleotide specific fluorescent properties.

The chemical synthesis of such a compound has already been described for the nucleotide dATP by Safarti et al., J. Biol. Chem. (1990), 265, pp. 18902–18906.

The existence of such a compound as well the existence of related compounds containing a fluorescent ester with different spectral properties {Hiraksuka (1982), J. Biol. Chem, 257, pp 13354–13358} suggests to a scientist skilled in the art that it is possible to esterify at position 3' "reporter" molecules which may be used for a sequencing procedure which is the subject of the present invention.

These esterified nucleoside triphosphates (3'-RT-dNTP) are substrates of the DNA or RNA polymerases which, when they are incorporated, lead to polynucleotide chain termination.

They lend themselves to three distinct reactions, namely incorporation by a nucleic acid polymerase into a growing chain, deprotection of the 3' hydroxyl of the deoxyribose making possible the incorporation of the next 3'-RT-dNTP. These properties can be used in a new non-radioactive method not based on the use of a gel to determine a nucleotide sequence or detect mutations in a DNA sequence.

One of the essential properties of these esterified nucleoside triphosphates is the in situ reversibility of this esterification making possible the restoration of the free 3' hydroxy groups, the polynucleotide chain being capable of undergoing further elongation on incubation with a mixture of dNTPs and DNA polymerase.

Since each nucleotide ester has fluorescent properties specific for a given base it is possible after removal and characterization of this fluorescent label to determine which of the nucleotide bases has been inserted.

The repetition of the procedure thus provides a method for the determination of a sequence of nucleotides or the detection of point mutations in a nucleotide sequence or the search for variants or finally the diagnosis of the presence of a particular oligonucleotide sequence in a sample.

The standard sequencing procedures were introduced about 15 years ago by Sanger, F., Nicklen, S and Coulson, A. R. {(1977) Proc. Natl. Acad. Sci. USA 74 pp. 5463–5467}, on the one hand, and by Maxam, A. M. and Gilbert, W {(1977) Proc. Natl. Acad. Sci. USA 74, pp. 560–564} on the other.

The dideoxy sequencing of Sanger is now widely used and is still the method of choice for determining a nucleotide sequence starting from a single stranded DNA matrix.

In brief, this method is the following: during the 4 enzymatic chain elongations the dideoxynucleotides are inserted at random in the place of the corresponding deoxynucleotide. The sequencing reactions generate a complex mixture which is then resolved by electrophoresis on polyacrylamide gel.

This method is relatively complex as regards the steps following the incorporation of the dideoxynucleotides, in particular with respect to the resolution on gel on the one hand and data acquisition, on the other.

In fact, a large diversity of products is generated by the elongation.

Various improvements were then made to this procedure with the objective of simplifying and reducing the experimental manipulations involved.

For example, in the patent application EP-O 531 169 A1, the authors developed a procedure making it possible to simplify and refine the electrophoresis step by using the techniques of pulsed field electrophoresis.

Other more recent improvements in the sequencing procedures have been described in the literature. We will mention two of them:

the "multiplex DNA sequencing" procedure {G. M. Church and S. Kieffer-Higgins, Science, 240, pp. 185–188 (1988)};

This procedure involves the formation of artificial genomes from a mixture of fragments inserted in multiple vectors adjacent to different labelled oligonucleotides; the DNA is subsequently cut chemically and subjected to electrophoresis then transferred to membranes and finally probed with oligonucleotides complementary to the labeled sequences in the vector;

the other well-known procedure was described in O. Ohara et al. Proc. Natl. Acad. Sci. USA, 86, pp. 6883–6887 (1989);

This procedure also uses gel and membrane systems making it possible to identify hybridized fragments with the oligomeric probes.

In the international patent application WO93/02212 the inventors describe a single step procedure for amplification and sequencing of DNA and RNA.

This procedure involves the use of nucleotide analogues of the deoxy type leading to chain termination in a repetitive manner, the separation of the reaction products being then made on polyacrylamide gel.

The sequencing technology is the subject of intensive studies, mainly because of the development of the projects on the genome. Many improvements are oriented towards several steps of the dideoxy method. Mention should be made, for example, of the articles of Venter, C. J. et al. {(1992) T.I.B.S. 10, pp. 8–11}, Prober, J. M. et al. {(1987) Science 238, pp. 336–341} and Mathies, R. A. and Huang, X. C. {(1992), Nature 359, pp. 167–169}.

Novel approaches are beginning to appear, such as sequencing by hybridization {Strezaska, Z et al. (1991) Proc. Natl. Acad. Sci. USA 88, pp. 10089–10093} or by scanning tunnelling microscopy {Driscoll, R. J. et al. (1990) Nature 346, pp 294–296}, methods which can be extensively developed if the gel electrophoresis is eliminated and replaced by a simple and quite cheap variant like that of the invention.

As for methods of identification of a nucleotide present at a defined position in a nucleic acid, the patent application WO93/02212 describes such a method of identification by incorporation of a dideoxynucleotide but this method, although it allows the detection of a point mutation, in no case permits the determination of a sequence in as much as no possibility is mentioned for restoring a normal nucleotide after incorporation of the modified nucleotide in the growing chain. Furthermore, it requires the placing of the probe next to the nucleotide concerned and does not enable more complex mutations such as small insertions or deletions to be characterized.

Finally, the manufacture and use of the dideoxynucleotides are expensive.

The patent application WO91/06678 describes a DNA method without gel and devices to implement this method.

The reaction involves dTNPs blocked at 3'. However, the enzymes mentioned and their mode of use—particularly the sequenase—do not allow the simultaneous use of nucleotides esterified at 3' nor the implementation of the procedure when the DNA to be sequenced exhibits repetitions of a given nucleotide; the sequenase possesses in fact an intrinsic esterase activity.

An ideal sequencing reaction would produce a single addition product in a controlled manner permitting the identification of the added nucleotide before repetition of the procedure leading to a stepwise determination of the sequence in real time.

The reversible protection of the 3' end of the DNA molecule being elongated might be a method conferring the desired properties for such a reaction. If, in addition, each nucleotide modified at the 3' end bears a distinct and individual label, it thus becomes possible to envisage the step by step determination of the sequence in real time.

The invention consists in the synthesis of novel derivatives of dNTPs or NTPs permitting their use as terminators of the growth of nucleic acid chains, it being possible to reverse this termination by chemical or enzymatic hydrolysis, in particular by an esterase, the step of the process being stable.

These derivatives may be advantageously used in any sequencing procedure such as that mentioned above characterized in that the procedure does or does not make use of a gel at any one of its steps.

The dNTPs or NTPs of the invention are more particularly characterized by the fact that they are esterified at 3' either by anthranilates or by caproic acid amidified by 4 different fluorophores each corresponding to a base or finally by 5-amine-2,5-dideoxy-D-ribonic acid or by 6-amino-2,3,6-trideoxy-D-gluconic acid, both also substituted at the amine function by 4 different fluorophores.

The four types of esters are represented by the following formulae I, II, III and IV:

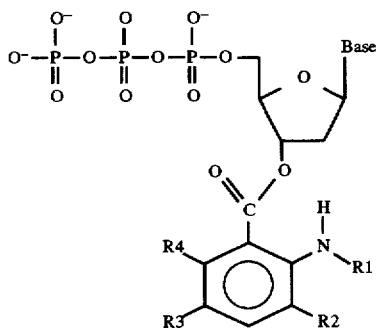

(I)

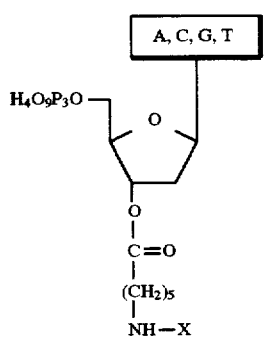

(II)

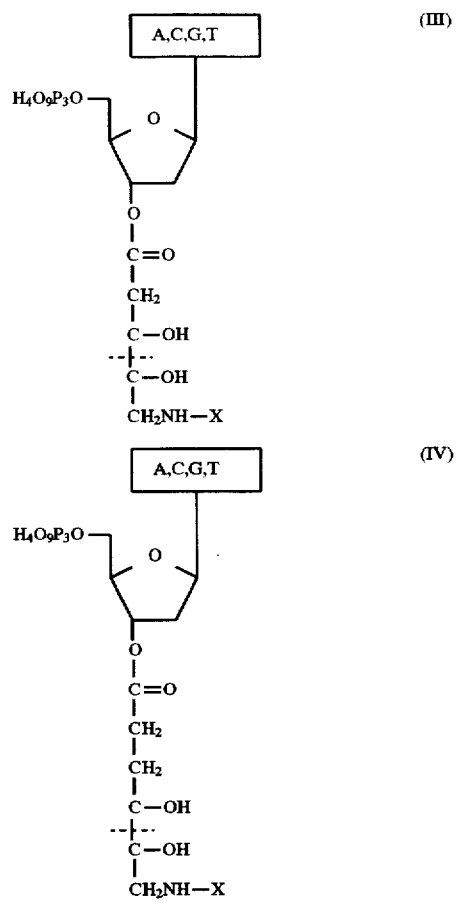

The restoration of the hydroxyl function at 3' of the sugar may be effected either by bases such as sodium hydroxide or also by the action of an enzyme in the case of the compounds of formula I and formula II. As for the compounds of formulae III and IV, the invention consists in cleavage of the fluorophore at a site 2 or 3 carbons removed from the 3' position of the nuleoctide.

This chemical reaction generates reactive groups which then produce a secondary reaction leading to the restoration of the hydroxyl at 3', namely two steps which are:

an oxidation of the vicinal diol by periodate, enolization, then a β-elimination of the aldehyde thus formed at 3' in the case of compound III, elimination as a result of the action of hydrazine in the case of compound IV (see details in FIG. 9).

The invention also relates to the procedure for the synthesis of these different classes of dNTPs esterified at 3' leading to the synthesis of the 4 esters exhibiting different fluorometric properties.

The invention also relates to the construction and use of a "hairpin" primer phosphorylated at 5' possessing a part of its 3' sequence identical with that of a primer used in PCR to produce the DNA matrix to be sequenced (see example below).

The term primer signifies any oligonucleotide sequence which, hybridized with a nucleic acid matrix, enables a polymerase to initiate the synthesis of the complementary strand.

A hairpin primer is covalently bound through its 3' end to the 5' end of the nucleic acid strand bearing the sought-after sequence.

The use of the "hairpin" primer makes it possible to use basic conditions for the deprotection of the 3' hydroxyl compatible with a repetition of the procedure without addition of a primer at each step of the indirect determination of a nucleotide inserted. In fact the rehybridization of the primer occurs intramolecularly and immediately.

Finally, the invention relates to the use of these esterified nucleotides in a method for the determination of a nucleotide sequence not based on the use of a gel. Said sequence may be amplified by the PCR technique beforehand.

These esterified nucleotides may also be used for the detection of point mutations or small mutations of the deletion or addition type, or finally for the search for variants in a given genetic sequence.

Finally, these modified nucleoside triphosphates may be used in a diagnostic method to detect the presence of a specific oligonucleotide sequence in a sample.

Finally, the invention relates to a diagnostic kit optionally containing a PCR primer, a sequencing primer, four 2'-deoxyribonucleotides reversibly esterified at 3', and optionally a solid phase to immobilize the target nucleic acid or primer, and finally a nucleic acid polymerase selected as a function of the primer.

DETAILED DESCRIPTION OF THE INVENTION

The invention is described in more detail in the description below accompanied by the Figures, the meaning of which is the following:

FIG. 1 represents the structure of the anthranilate esters in which R1 to R4 represent either a —H group or a —$CH_3$ group depending on the 3'-RT-dNTP considered:

3'-Ant-dATP: R1=R2=R3=R4=H

N-methyl-3'-Ant-dCTP: R1=$CH_3$; R2=R3=R4=H 3-methyl-3'-Ant-dTTP: R1=R3=R4=H; R2=$CH_3$ and 5-methyl-3'-Ant-dCTP: R1=R2=R4=H; R3=$CH_3$ Any other combination of substituent groups on the anthranilic ring also form part of the invention.

Figure 10A:
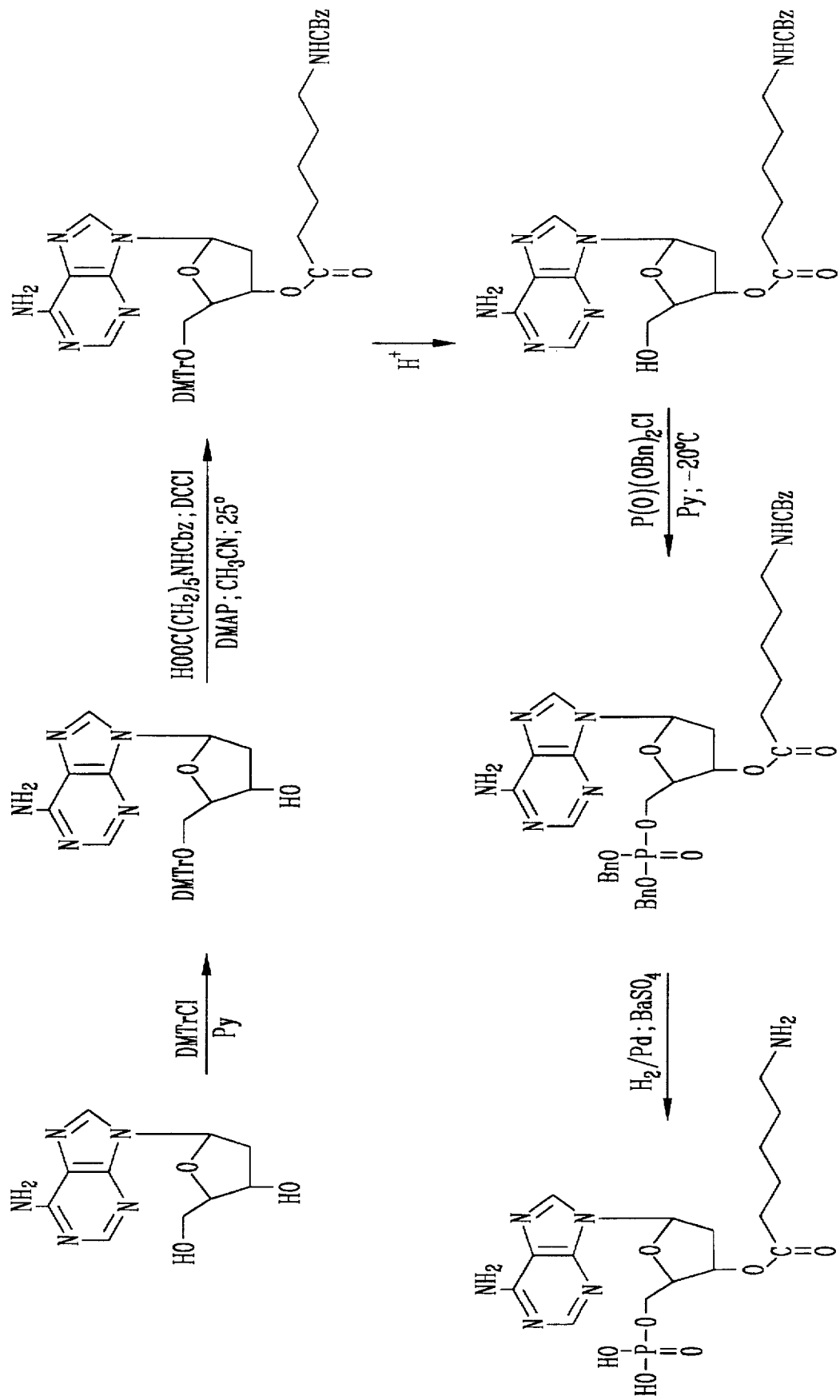
Figure 10B:
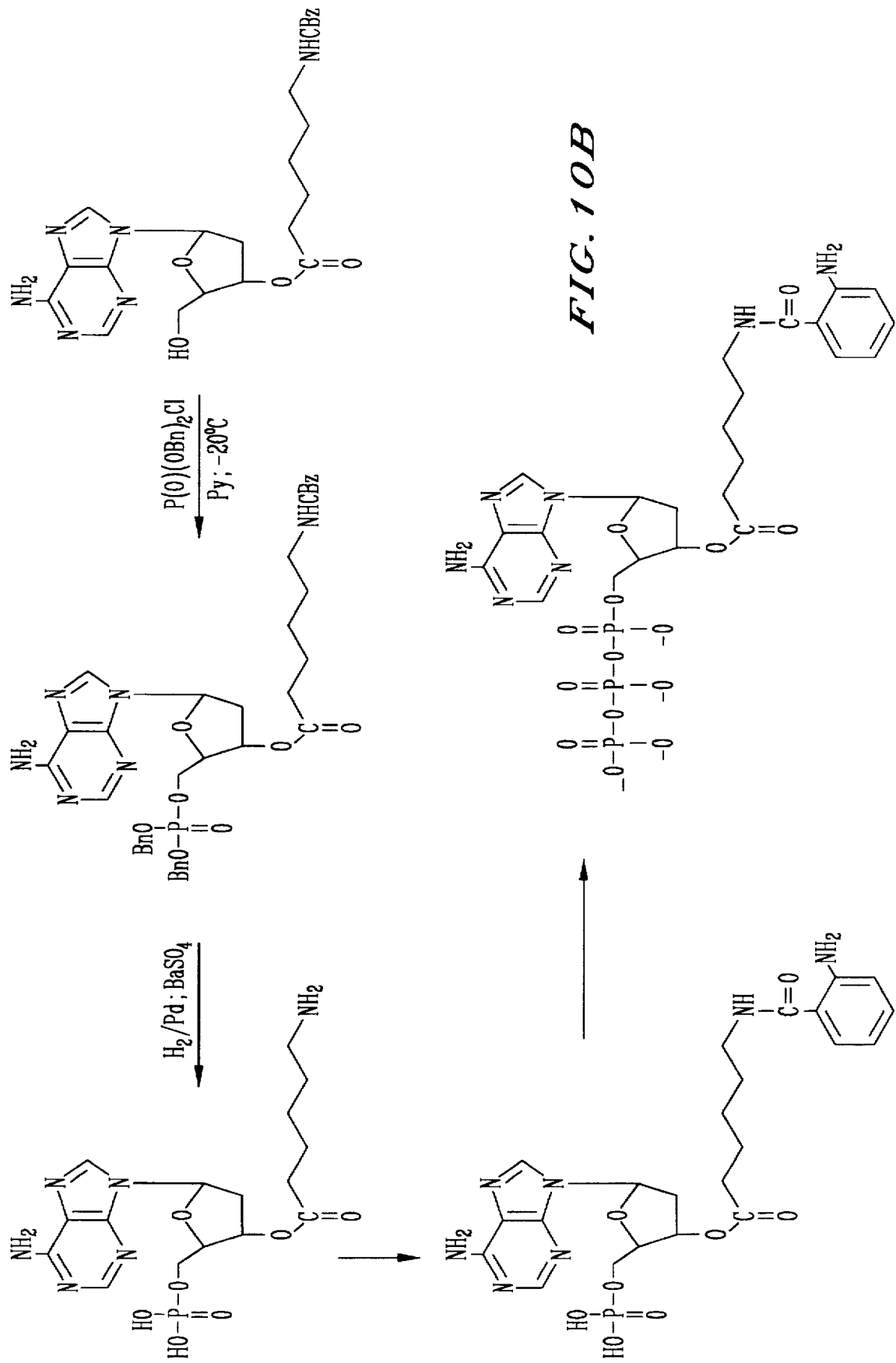
Figure 11A:
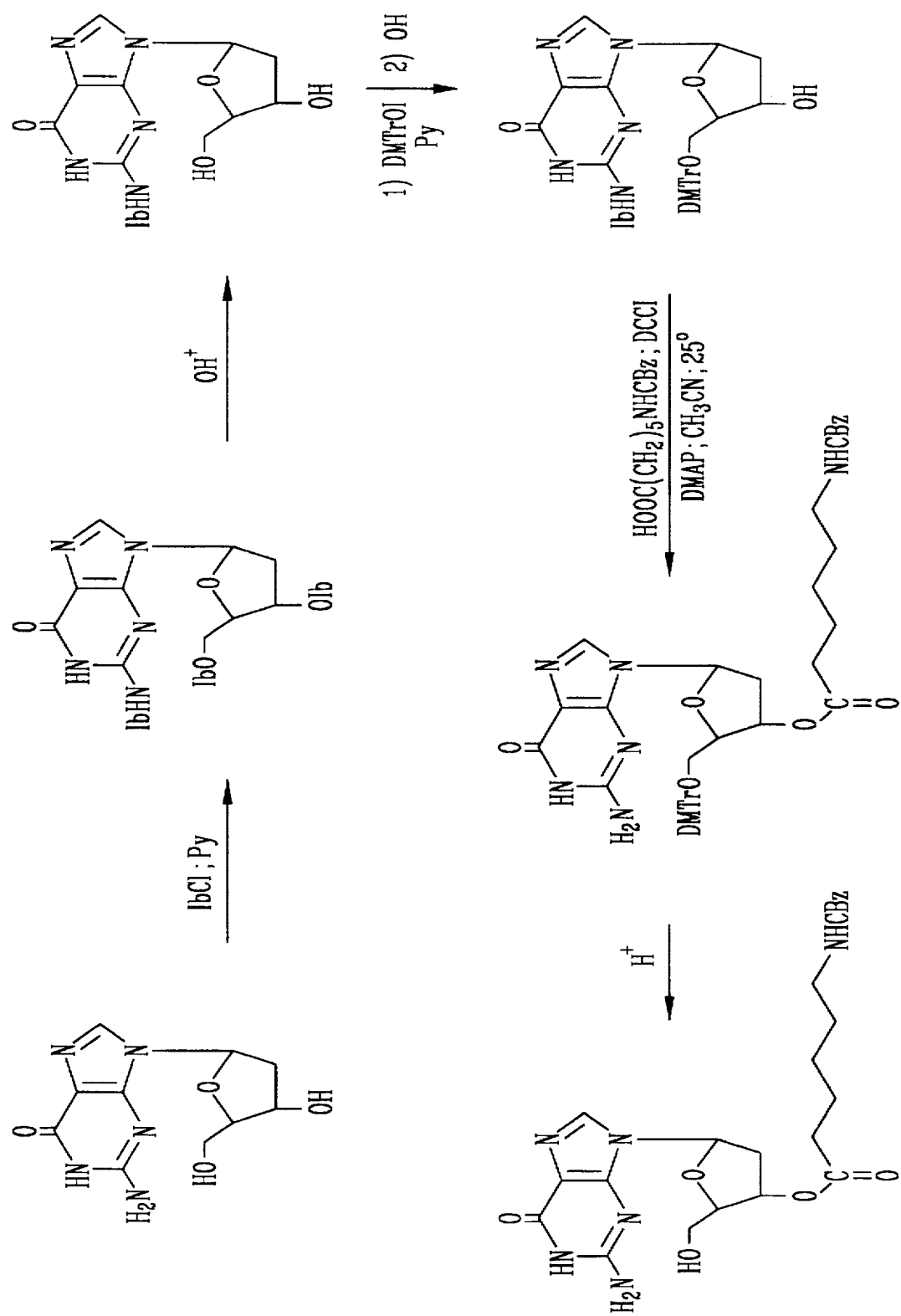
Figure 11B:
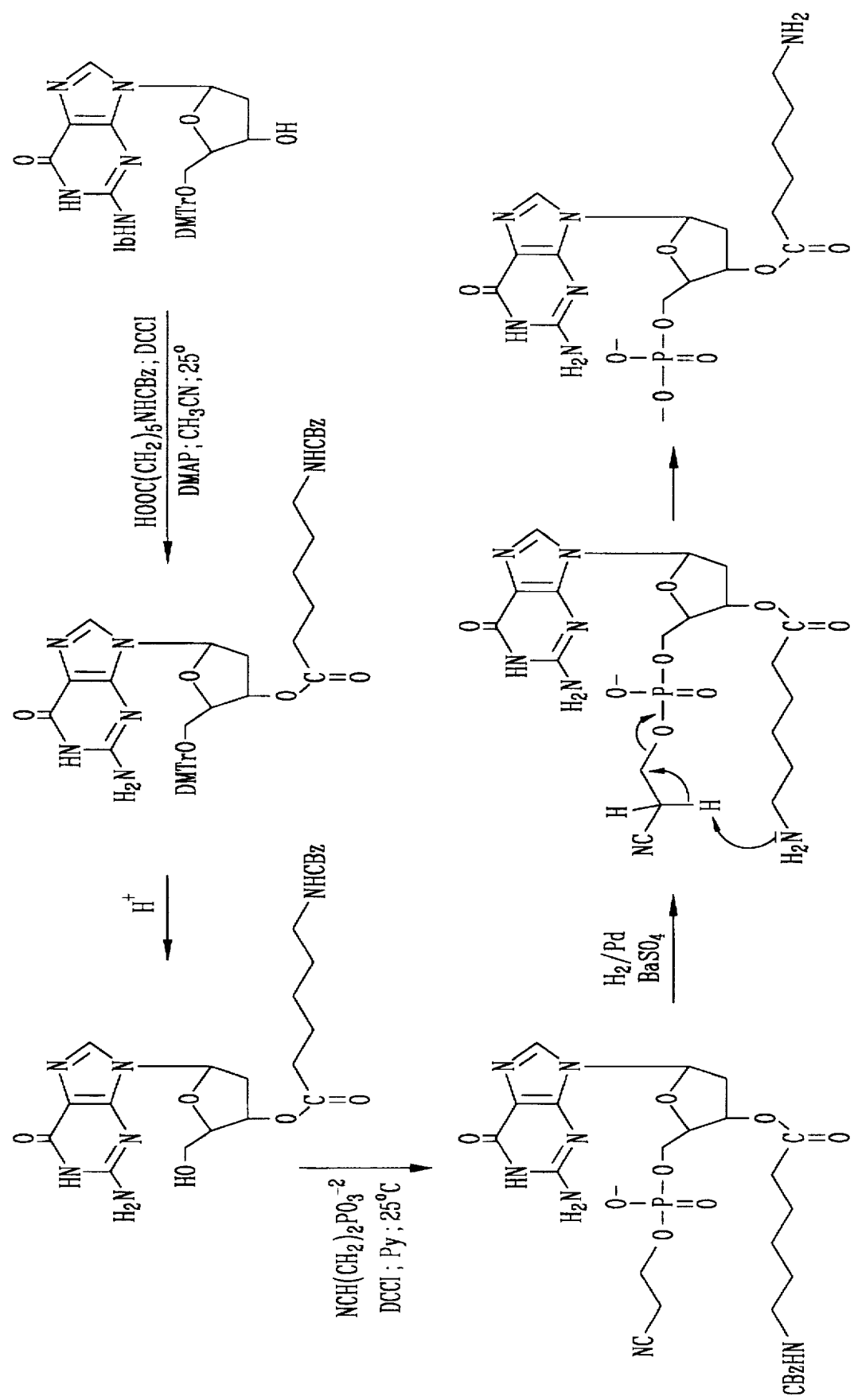
Figure 11C:
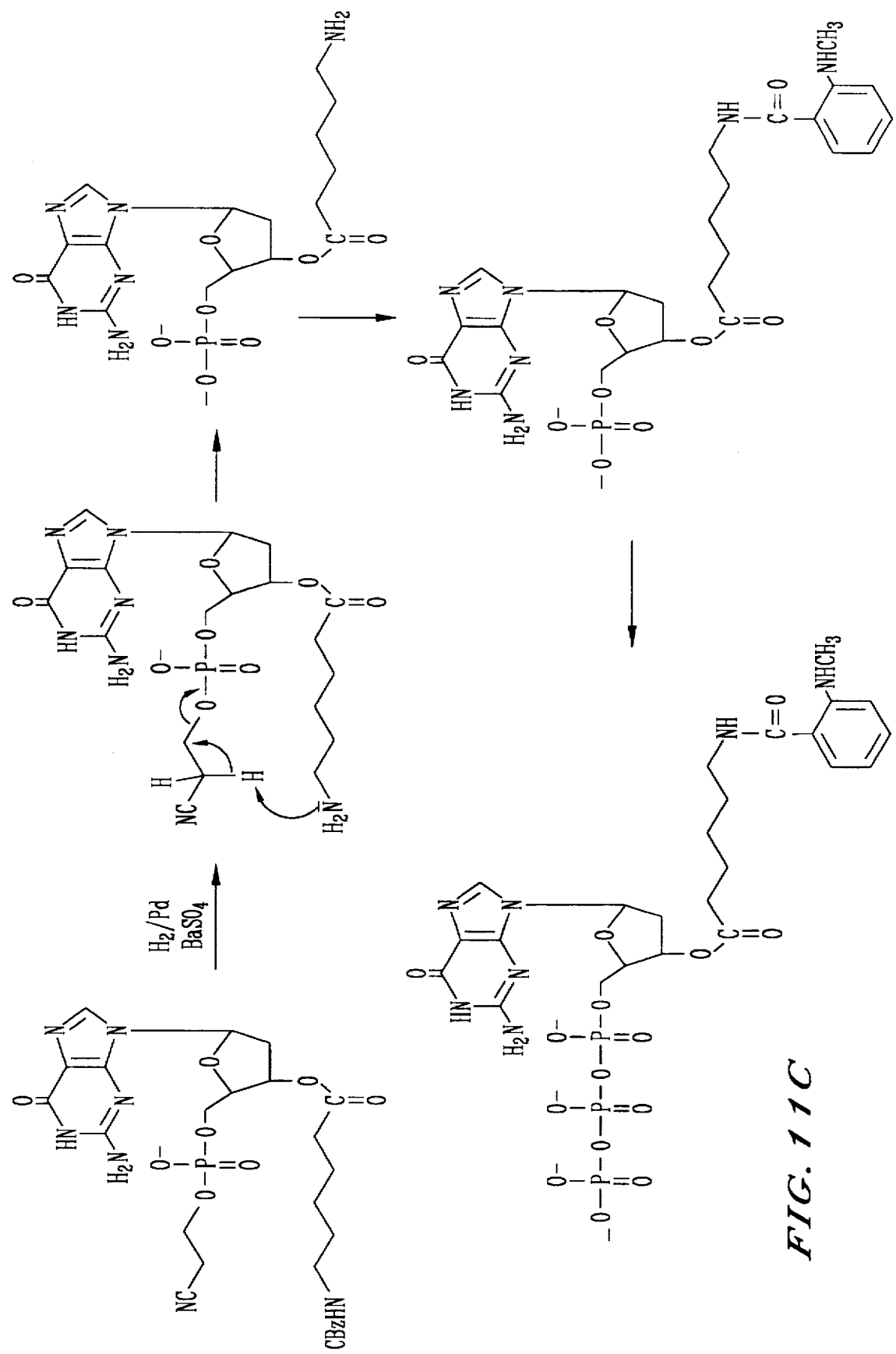

FIGS. 10 and 11 show respectively the schemes far the synthesis of the 2'-deoxyadenosine and 2'-deoxyguanosine triphosphates acylated at 3' by 6-aminocaproic acid substituted by a fluorochrome.

The materials and methods used are the following:

Substances for the synthesis of the derivatives:

Isatoic anhydride, N-methylisatoic anhydride, 2-amino-3-methyl-benzoic acid, 2-amino-5-methyl-benzoic acid and 2-amino-6-methyl-benzoic acid are obtained from Aldrich. The corresponding anhydrides were prepared by the action of phosgene or ethyl chloroformate on the adds (Erdmann). The nucleocide triphosphates dATP, dGTP, dTTP and dCrP are obtained from Boehninger Mannheim.

Incorporation reaction:

The modified DNA polymerase lacking exonuclease (Sequenase 2.0) is obtained from the USB Corp. (USA). The 2', 3'-dideoxynucleoside/2'-deoxynucleoside-5'-triphosphates, AMV-reverse transcriptase, M-MuLV reverse transcriptase are obtained from Boehringer (FRA). The T7 DNA polymerase is supplied by Pharmacia (France), the Klenow enzyme is obtained Amersham (France). One unit is the enzymatic activity which incorporates 1.0 nmole of total nucleotides in a product insoluble in acid in 1 minute at 37° C. with poly (d(A-T)) as matrix.

Magnetic beads coated with streptavidin (M-280 Dynabeads) are supplied by Dynal (Norway). α-$^{32}$P-dCTP (3000 Ci/mmole), α-$^{35}$S-dATP (600 Ci/mmole), $^3$H-dGTP (14 Ci/mmole), $^3$H-dCTP (17 Ci/mmole), $^3$H-dTTP (45 Ci/mmole) are obtained from Amersham (France).

The oligonucleotides are synthesized with an ABI synthesizer and purified before use.

Spectral measurements:

The absorption spectra are recorded at 25° C. in a double beam spectrophotometer in the presence of 50 mM Tris-HCl (pH 8.0). The fluorescence emission spectra and the excitation spectra are measured at 25° C. in a Perkin-Elmei LS50B fluorescence spectrophotometer. All of the free acid derivatives are excited at 310 nm whereas the 3'-anthraniloyl and 3'-methylanthraniloyl derivatives of the deoxynucleotides are exited at 330 nm. The slit widths for excitation and emission are 2.5 nm.

Figure 1:
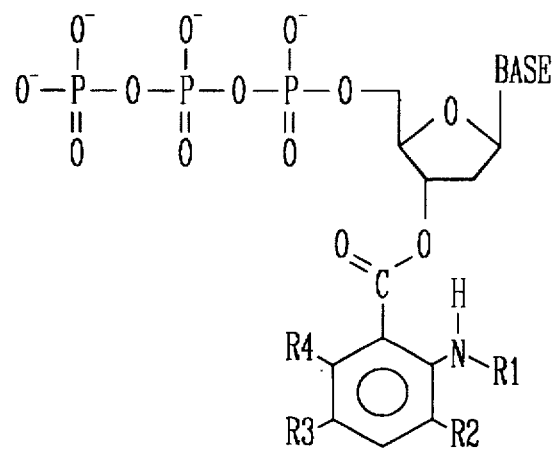

The absorption and emission wavelengths for each of these anthraniloyl dNTP derivatives, compared with those of the unsubstituted derivatives, are summarized in the following Table I in which R1, R2, R3 and R4 correspond to the residues of FIG. 1.

TABLE 1

| | | | | Free Acids | | 3'-RT- dNTP | | |
|---|---|---|---|---|---|---|---|---|
| R1 | R2 | R3 | R4 | $\lambda_{max}$* absorption | $\lambda max$* emission | dNTP | $\lambda_{max}$* absorption | $\lambda max$* emission |
| H | H | H | H | 315 | 396.5 | dATP | 333 | 427 |
| $CH_3$ | H | H | H | | 416.5 | dGTP | 356 | 444 |
| H | $CH_3$ | H | H | 312 | 403 | dCTP | | 432 |

TABLE 1-continued

| | Free Acids | | | | | 3'-RT- dNTP | | |
|---|---|---|---|---|---|---|---|---|
| R1 | R2 | R3 | R4 | $\lambda_{max}$* absorption | $\lambda$max* emission | dNTP | $\lambda_{max}$* absorption | $\lambda$max* emission |
| H | H | CH$_3$ | H | 317 | 409 | dCTP | | |
| H | H | H | CH$_3$ | 289 | 403 | dTTP | | 435 |

Synthesis, purification and characterization of the 2'-deoxynucleoside-5'-triphosphates reversibly labelled at 3' (3'-RT-dNTPs):

a) Anthranilate dATP:

Anthranilate dATP was prepared from dATP and isatoic anhydride by a procedure similar to that described by Hiratsuka {T. Hiratsuka (1982) J. Biol. Chem 257, pp. 13354–13358} for the synthesis of the anthranilate ATP and was purified by chromatography on Lichroprep RP18 (25–40 μm) using 1 mM triethylammonium acetate as eluent.

The unreacted dATP is eluted first. The Ant-dATP is then eluted with a mixture of 1 mM triethylammonium acetate and acetonitrile (9:1 v/v). The fractions containing the pure Ant-dATP are assayed in thin layer chromatography on silica gels using as solvent the mixture CHCl$_2$/MeOH/NH$_4$OH (65:35:10, v/v/v),then lyophilized.

20 mg of pure nuleoctide (0.032 mol) are obtained starting from 24 mg of dATP (0.04 mol), which represents a final yield of 80%.

The identity and purity of the compound are verified by UV spectrophotometry ($A_{253}/A_{333}$=4.3, $\xi^{253}$ mM=20) by mass spectrometry (FAB+) M+ 610, m/e 611, (M+H)+.

The spectral properties of the product in proton and phosphorus NMR at 300 MHz are the following: (300 MHz; D2O) 8.44 (s', 1H, H-8), 8.11 (s, 1H, H-2), 7.83 (d, 1H, H-6A), 7.24 (t, 1H, H-4A), 6.72 (d, 1H, H-3A), 6.66 (t, 1H H-5A), 6.48 (dd, 1H, H-1), 5.62 (dd, 1H, H-3'), 4.38 (m, 1H, H-4'), 4.19 (m, 1H, H-5'), 4.09 (m, 1H, H-5"), 2.83 (m, 1H, H-2'), 2.69 (m, 1H, H-2"). $^3$P (121.5 MH2; D2O) −10.02 (d, Pδ), −10.84 (d, Pα), −22.48 (t, Pβ).

b) Anthranilates of dCTP, dGTP and dTTP:

The synthesis, purification and characterization were carried out by similar methods.

The 3-methyl, 5-methyl and 6-methyl isatoic anhydrides were prepared by the procedure described by Erdmann {E. Erdmann (1899) Berichte 3, pp. 2159–2172}.

Figure 2:
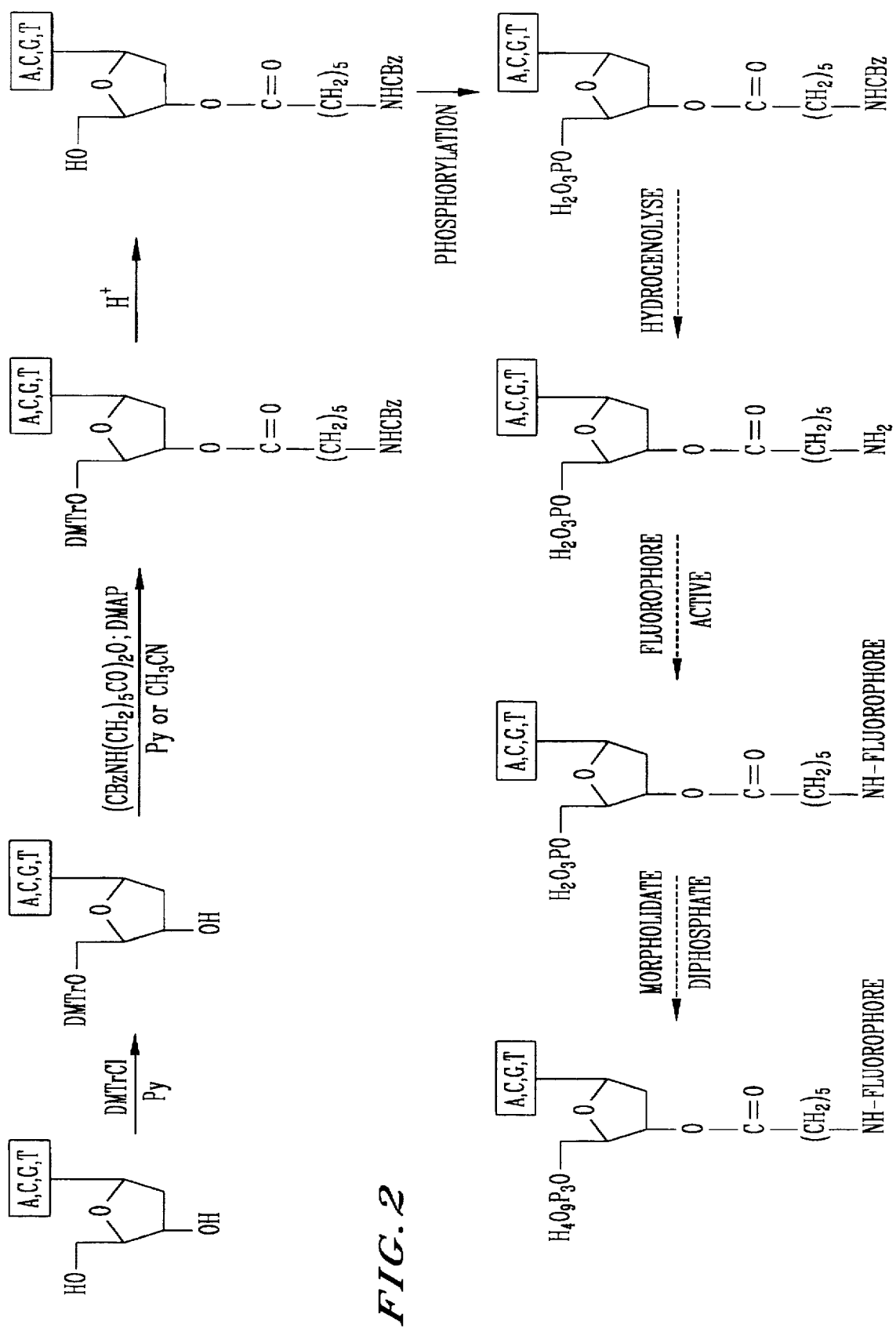
FIG. 2 shows the structure of the caproic acid esters, and a synthetic route to these esters.

Their spectral properties have also bee measured as well as those of N-methyl Ant-dGTP, 3-methyl Ant-dCTP, 6-methyl dTTP and 5-methyl Ant-dCTP.

c) Synthesis of the esters of dNTPs and caproic acid, amidated by the fluorophores:

The scheme is shown in FIG. 2.

The hydroxyl at 5' of the 2'-deoxynucleoside is protected by a dimethoytrityl group and the alcohol at position 3' is esterified by the action of caproic acid anhydride, the amine of which has been previously locked by the benzyloxycarbonyl. The primary alcohol at 5' is deprotected in weakly acidic medium, then phosphorylated. The amine function of the caproic ester is deprotected by hydrogenolysis, then substituted by the fluorophore.

In a last step, the monophosphate activated in the phosphoroimidazolate form is converted into the triphosphate by the action with the tetra- tri-n-butylammonium salt of pyrophosphoric acid.

d) Synthesis of the purine triphosphates acylated at 3' by 6-amino-caproic acid substituted by different fluorochromes:

2'-deoxyadenosine (FIG. 10):

The 5' hydroxyl of 2-deoxyadenosine acylated at 3' is phosphorylated by dibenzyl phosphorochloridate; the phosphate and the amine are deprotected by hydrogenolysis.

2'-deoxyguanosine (FIG. 11):

The case of 2'-deoxyguanosine is special; in fact, dibenzyl phosphorochloridate does not react with the 5' OH. It was phosphorylated by action of cyanoethylphosphate in the presence of dicyclocarbodiimide During the hydrogenolysis of the benzyloxycarbonyl group the phosphodiester is converted into the phosphomonoester by intramolecular elimination of the cyanoethyl group. A scheme of synthesis is shown in FIG. 11.

Incorporation of the 3'-RT-dNTPs:

About 2 picomoles of a 5'-biotinylated 21-mer (5'-bio-ATACTTTAAGGATATGTATCC - 3') are bound to M-280 Dynabeads in the manner described by the manufacturer and hybridized with an excess (about 50 pmoles) of a complementary oligonucleotide exhibiting a 5' tail (dT)$_{10}$, (dC)$_5$, (dG)$_5$ or (dA)$_5$. The hybridization is done for one hour at room temperature in the presence of 1M NaCl, 5 mM Tris-HCl (pH 7.5) and 0.5 mM EDTA. After removal of the unbound oligonucleotide, the washed beads are suspended in a buffer supplied by the manufacturer and incubated in the presence of 500 μM of a unique 3'-RT-dNTP and DNA polymerase at 50° C. The reaction is terminated by 20 mM EDTA, 0.01% Triton X-100, the beads are washed and their concentration determined under a microscope with a hemacytometer cell before being assayed to determine the incorporation of radioactivity (see below).

Figure 4:
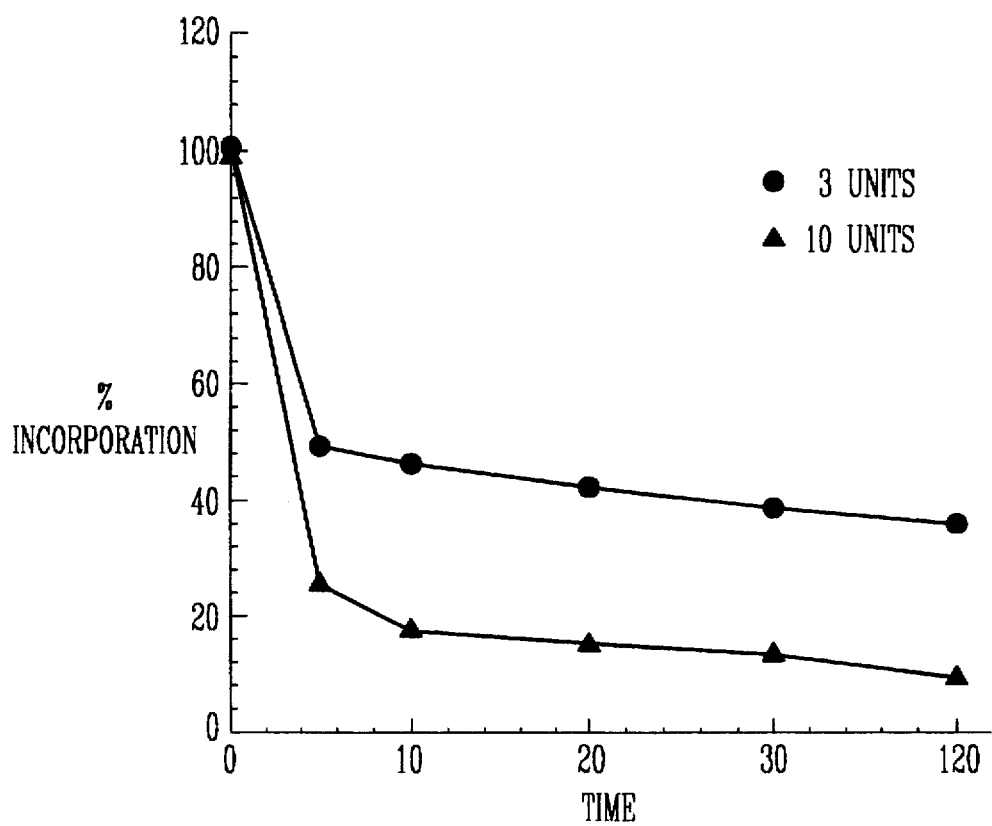
FIG. 4 shows the kinetics of incorporation of the 3'-Ant dATP derivatives into a growing chain as a function of different quantities of DNA polymerase.

As these nucleotide analogues do not contain a 3'-hydroxy group, their incorporation into a growing DNA strand results in chain termination. This is shown in FIG. 4, in which a DNA substrate is first treated with a 3'-RT-dATP and the Taq DNA polymerase for different periods of time before being washed and assayed in order to determine the free 3' hydroxy groups available for chain elongation.

Under these conditions about 80% of the DNA substrate are blocked for additional elongation in 10 minutes with 10 units of enzyme, then there is a regular, slow diminution a the quantity of available 3' hydroxy groups. When the 3'-RT-dGTP, 3'-RT-dTTP or 3'-RT-dCTP are tested with their respective matrices, similar profiles are obtained. If a given 3'-RT-dNTP is incubated with a DNA polymerase and a matrix with which it does not correctly base pair, subsequent chain termination is not observed, which indicates that the 3' group does not modify the recognition mechanism of the enzyme.

These results show that in spite of a relatively voluminous 3' group, these modified nucleotides are still accepted by the enzyme. Very many chain termination nucleotide analogues are substrates for different DNA polymerases. It has been shown that correct base pairing of the nucleotide substrate with its DNA strand serving as matrix and the formation of a phosphodiester bond seem to occur even with enantiomers of β-L-ribosides {Van Draanen, N. et al. (1992) J. Biol. Chem. 267, pp. 25019–25024}, which indicates that the binding of the sugar portion by the enzyme is probably not specific.

The modified nucleotides of the invention are in addition accepted as substrates by several DNA polymerases.

Figure 5:
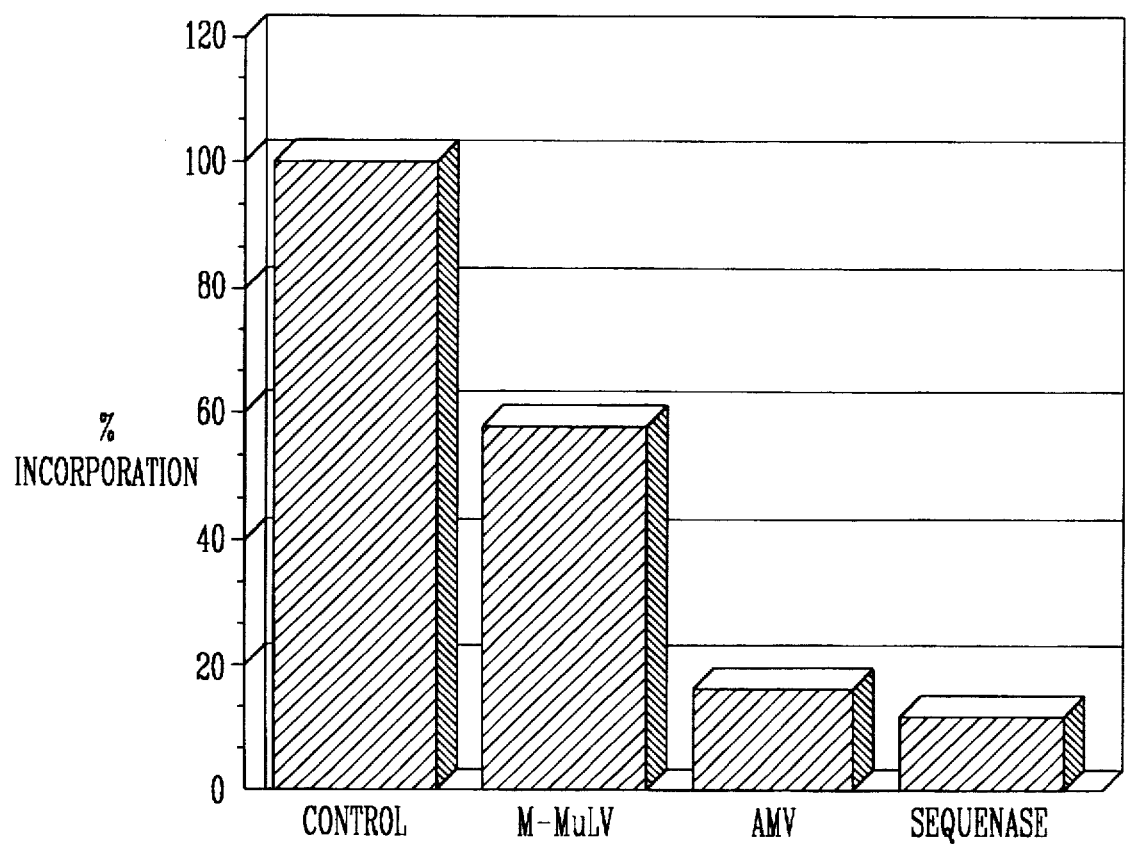
FIG. 5 shows the in cation of the 3'-Ant dATP in the presence of different DNA polymerases—the incubation is performed for 60 minutes at 37° C. with one unit of each enzyme.
Figure 6:
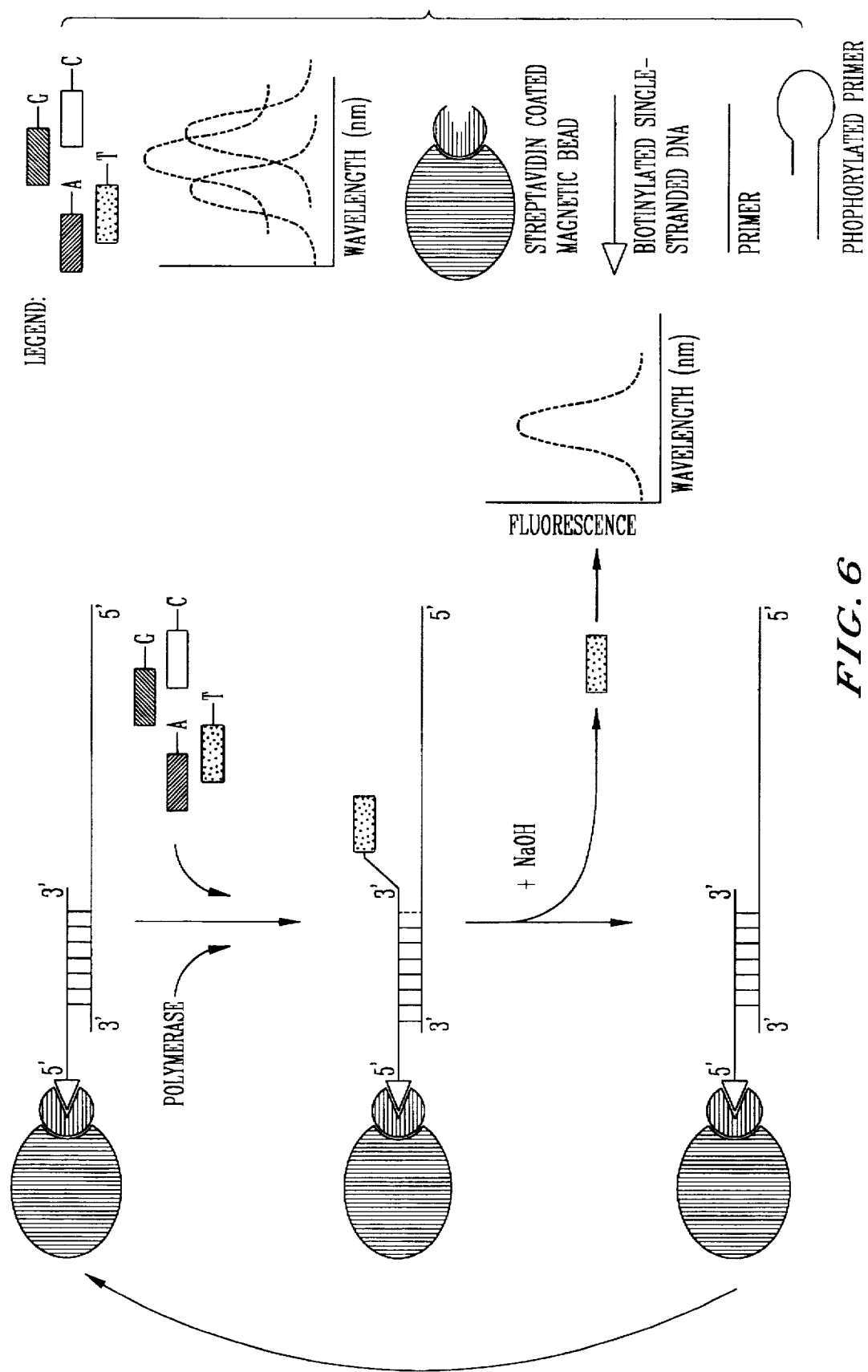
FIGS. 6, 7 and 8 show three variants of the sequencing method using the 3'-RT-dNTP of the invention in which the symbols have the meaning indicated below FIG. 6.
Figure 7:
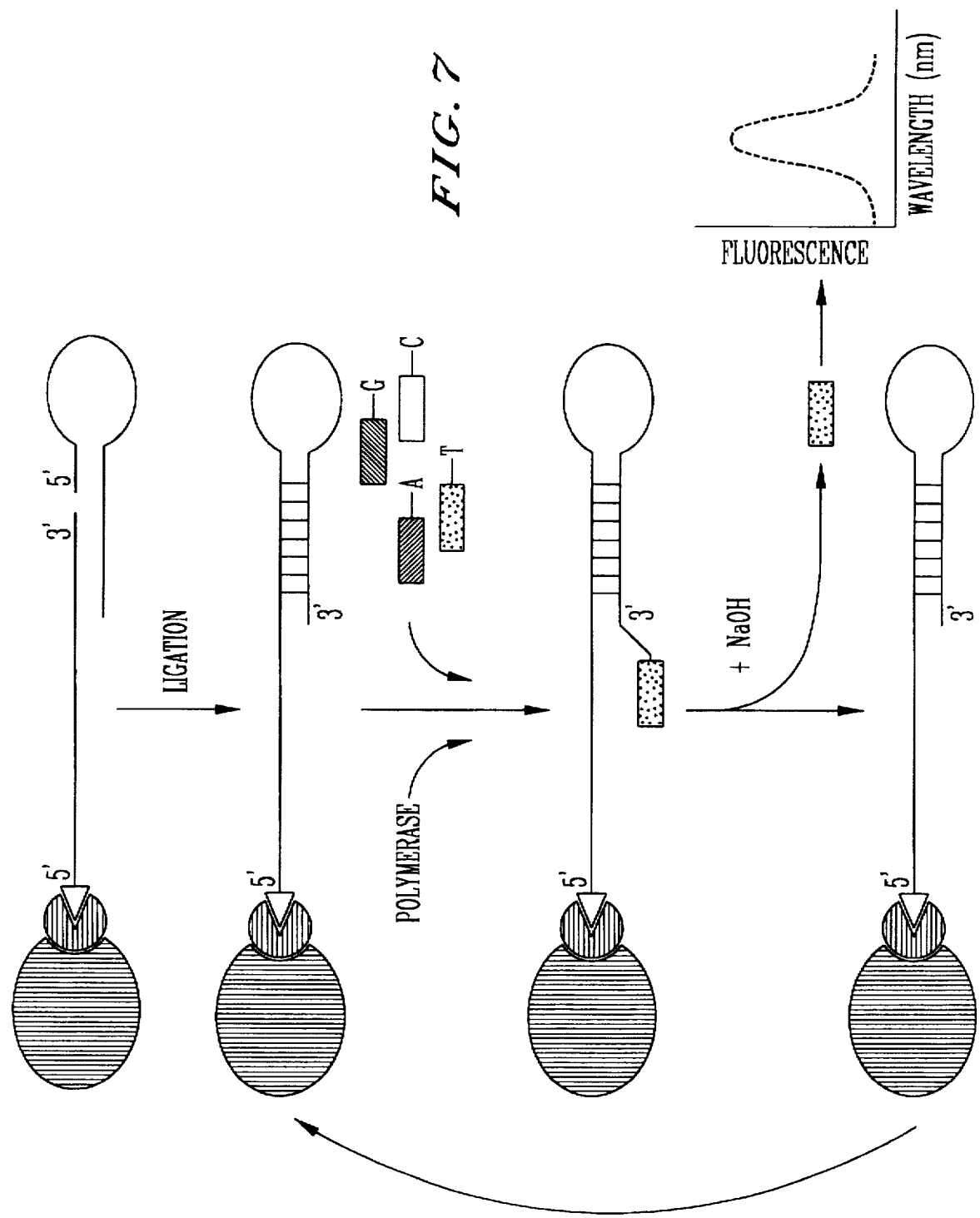
Figure 8:
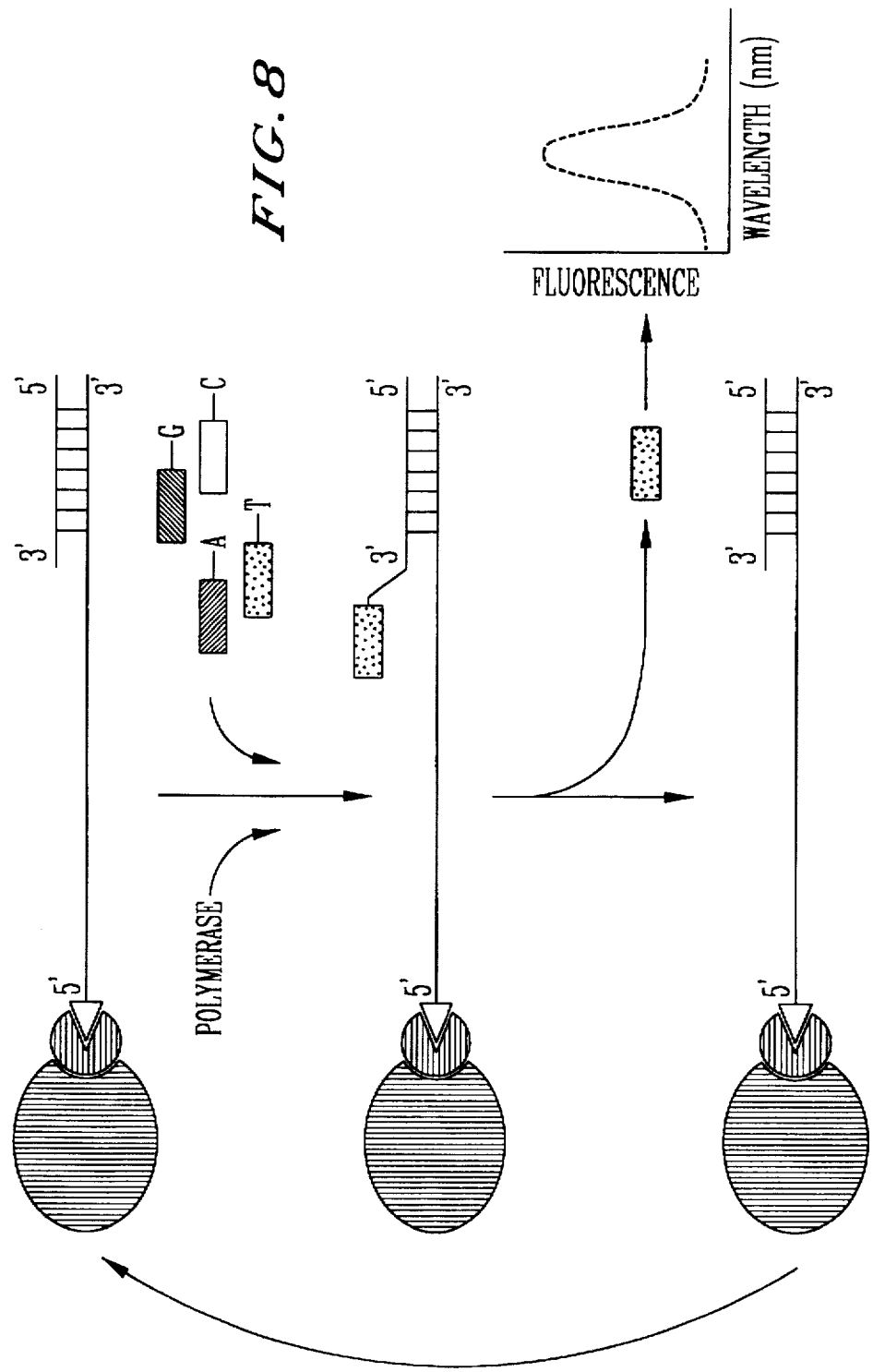

FIG. 5 shows that analogues synthesized here are substrates for different polymerases, the sequenase and the M-MuLV reverse transcriptase being respectively the most and the least efficient under the assay conditions used here. An unmodified T7 DNA polymerases, a Taq polymerase and Klenow fragment of commercial DNA polymerase I are also capable of using these substrates. The applicant has not tried to optimize the incorporation with a given DNA polymerase as regards the 3'→5' exonuclease activity, the suitability to the treatment as a function of distribution along the chain, or the condensation kinetics.

However, it seems clear that the procedure can be repeated for the next base only if the enzyme efficiently condenses the nuleoctide at 3' and does not possess 3'→5' exo activity which can remove the newly condensed nuleoctide.

It also seems to be crucial for the procedure described here that the DNA polymerase does not possess intrinsic esterase activity in its polypeptide chain.

Such an activity does exist in the Klenow fragment and in the modified or unmodified T7 DNA polymerases.

This activity is independent of the degree of purification of the enzyme and hence borne by the same protein as that possessing the polymerase activity.

As this esterase activity is exercised during polymerization when a nuleoctide is paired correctly and esterified at 3', this esterase activity makes it impossible to control chain termination when the four 3'-RT-dNTPs are used at the same time.

However, the Taq DNA polymerase does not possess this esterase activity under certain reaction conditions like those described here and is hence the enzyme of choice for the sequencing procedure described below.

Removal of the fluorescent markers and restoration of the 3' hydroxyl:

a) Anthranilate esters:

At this step, a label borne at 3' by the inserted nuleoctide would have two major roles: that of establishing a distinction between the four possible nucleoside bases inserted and of blocking a subsequent elongation procedure The removal of the label will provide an indirect identification of the base inserted as well as the regeneration of a free 3' hydroxy group available for the repetition of the procedure.

The nature of the chemical ink between the ribosyl part and the anthraniloyl substituents is particularly important. The carboxylic esters are easily hydrolysed by equivalent quantities of hydroxide ions compatible with the chemical stability of the single stranded DNAs {Nucleic Acid Chemistry, Townsend, L. B. and Tipson, S. R. eds, John Wiley and Son, New York and Jencks, W. P. (1969) Catalysis in Chemistry and Enzymology, Dover Publications, Inc., New York}. Furthermore many different esterases and serine proteases catalyse the hydrolysis of a large variety of these esters {Heymann, E. and Mentlein, R. (1981) Methods Enzymol. 77, pp. 333–344} as does proteinase K on a 3'-anthraniloyl-2'-dAMP of the type I and II described on page 5 It might be possible to esterify position 3' with a label bearing a spacer arm designed specifically to be easily and efficiently removed either enzymatically or chemically.

Subsequently, the 3'-RT-dAMP is added to the free 3'-hydroxy group of a DNA matrix as described above and the carboxylic ester is then hydrolyzed with 0.1M sodium hydroxide for 5 minutes at 37° C. (Table 2). After re-hybridization of the complementary strand the DNA polymerase can incorporate between 83 and 103% of radioactivity as compared with the same matrix which was not blocked at 3'. The fact that 100% are not always recovered probably results from an incomplete re-hybridization of the oligonucleotide rather than from harsh alkaline treatment. Analogous conditions of hydrolysis of a ribosyl ester have been reported by others {Falbriard, J. G., Posternak, T. and Sutherland, E. W. (1967) Biochim. Biophys. Acta 148, pp. 99–105 and Hiratsuka, T. (1982) J. Biol. Chem. 257, pp. 13354–13358}. The applicant has not deserved an appreciable difference of efficiency of ester hydrolysis between the four 3'-RT-dNTPs incorporated.

b) Caproic acid esters:

The release of caproic acid substituted by the fluorophore is carried out by the action of an enzyme, for example a lipase or a hydrolase.

Figure 9:
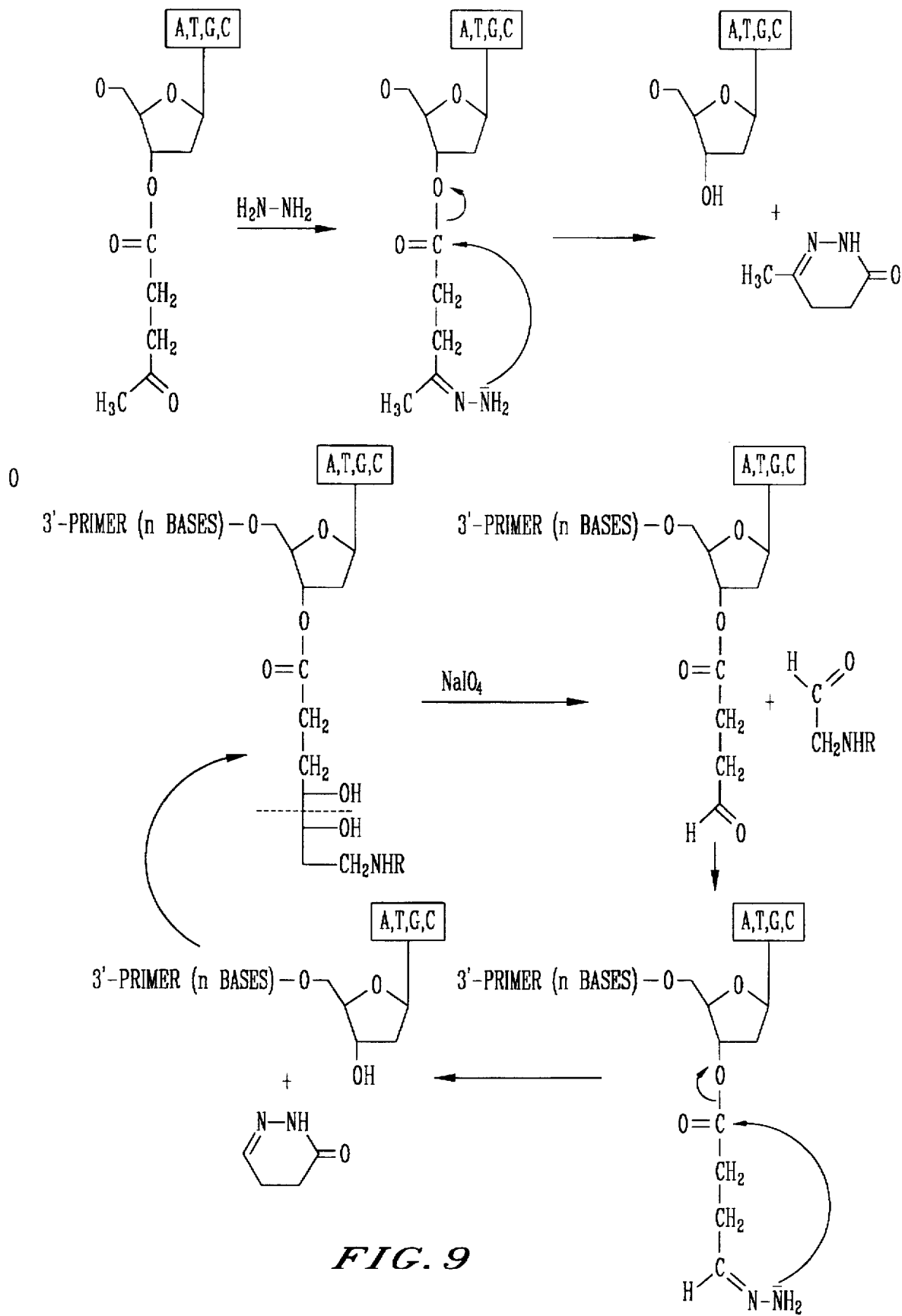
FIG. 9 shows the mechanism of release of the label and of the 3' hydroxyl from the 2'-deoxynucleoside triphosphates acylated at 3' by 6-amino-2,3,6-trideoxy-D-gluconic substituted on the amine function by different fluorochromes.

In order to facilitate the deprotection of the phosphate in particular for application to larger quantities of products we have focussed on another method which uses as phosphorylating agent (P. T. Gilham and H. G. Khorana, J.A.C.S. 80, 6212–6222), dibenzyl phosphorochloridate (compound B; FIG. 9). Although it is quite limiting (48%) for the synthesis, this solution offers a not insignificant advantage. In fact, starting from compound (11) compound (12) is obtained in a single hydrogenolysis step carried out under mild conditions (room temperature and atmospheric pressure).

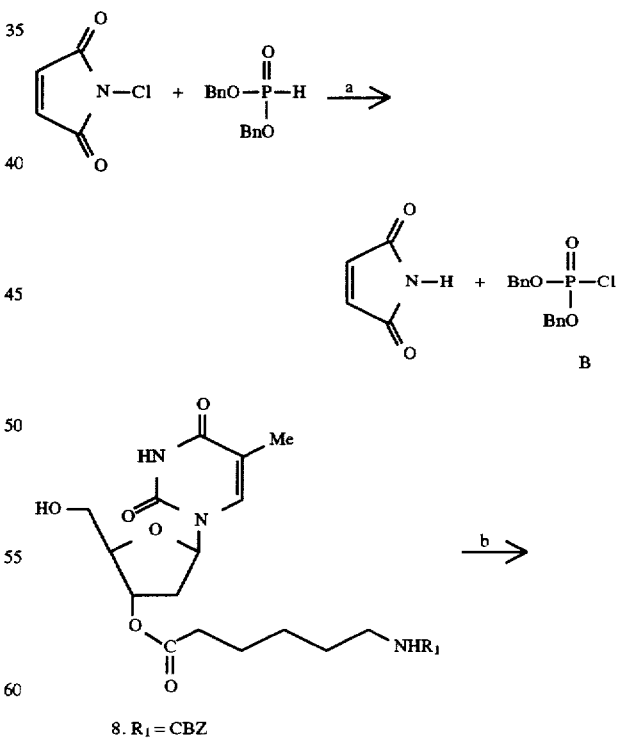

8. R₁ = CBZ

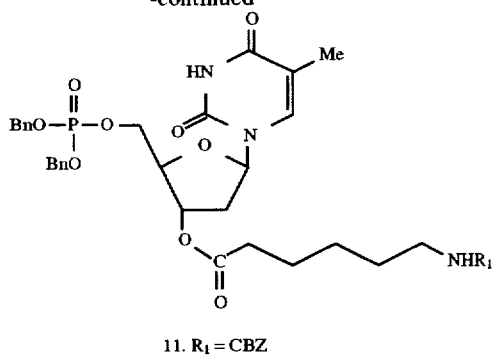

11. R₁ = CBZ

↓ c

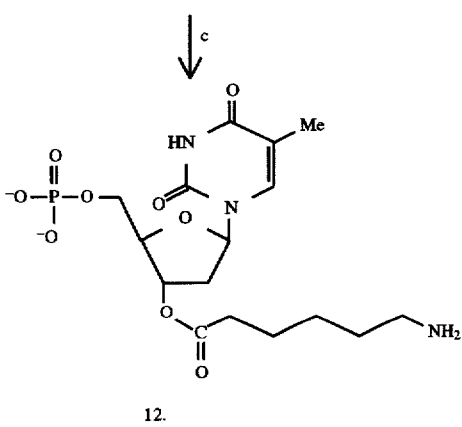

12.

(a): toluene; N₂; 25° C.
(b): B; pyridine; N₂; -20° C.
(c): Pd/BaSO₄; H₂; 90% EtOH We have tried several experimental conditions for the deprotection of compound (11) by hydrogenolysis (P. T. Gilham and H. G. Khorana; J.A.C.S. 1958, 80 6212–6222):
several solvents; ethyl acetate, ethanol, 90% ethanol and tetrahydrofuran;
two catalysts; palladium on charcoal and on barium sulphate.

90% Ethanol in the presence of palladium on barium sulfate has proved to be the ideal solvent. In fact, in the latter, complete deprotection (loss of the benzyls and the benzyloxycarbonyl) is quantitative and the isolation of the phosphomonoester esterified at 3' (compound 12) is quite easy.

We have chosen to assign fluorescein as label to thymidine (INTERBIOtech Molecular Probe; "1992–1994 Handbook of fluorescent probes and research chemicals" 1992, 20–41) (FITC), the latter complying with the criteria previously established:

non-radioactive label;

absorption ($\xi=76\times10^{-3}$ l; $\text{mol}^{-1}.\text{cm}^{-1}$ at $\lambda_{max}$=495 nm in DMF and at pH=9 and emission at $\lambda_{max}$=519 nm, both high values.

In general, an amine function reacts with an isothiocyanate function at a pH lose to 11 (this reaction has already been carried out in the laboratory (S. R. Sarfati and A. Namane, Tet. Let. 1990, 31, 2581–2584). Now we know that at this pH the aliphatic chain grafted at 3' is hydrolyzed. To offset this disadvantage, we allow compound (12) to react with 5-isothiocyanate fluorescein in a pyridine/water mixture at room temperature. These conditions have been described for 6-aminocaproic acid and 5-isothiocyanate-fluorescein by F. S. Wusteman and P. Gacesa (Carbohydrates Research, 1993, 241, 237–244) (scheme below).

This method has led both to our not observing the formation of TMP that occurs in alkaline medium and to our recovering the fraction of the compound (12) which had not reacted. Furthermore, the difficulties which we have encountered with respect to the solubility of the product have induced us to evaluate the yield by high performance liquid chromatography (HPLC) on a reversed phase column and to purify by this means only the quantity necessary for the characterization of the product.

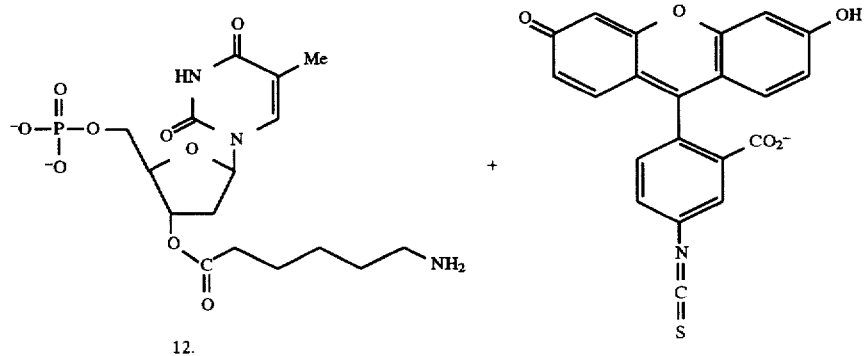

12.

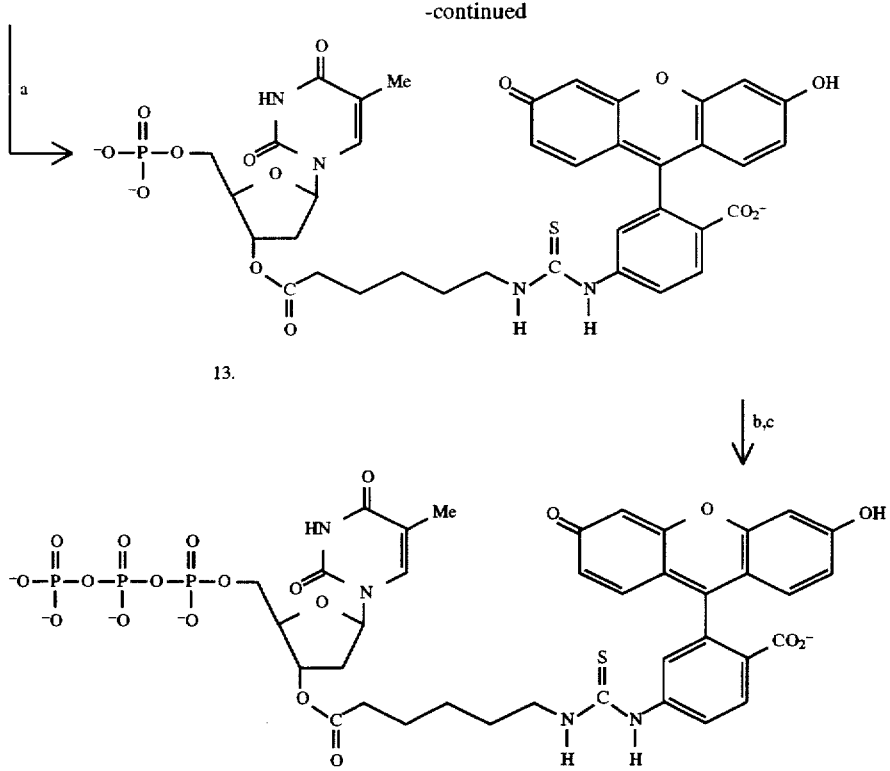

13.

14

(a): pyridine/water; 25° C.
(b): carbonyldiimidazole; DMF; 25° C.
(c): $P_2O_7^{-4}$ $(Bu_3N^+H)_4$; DMF; 25° C.

Starting from compound (13) we had the choice between two possibilities for preparing the triphosphate of the thymidine analogue (compound 14). A first method consists of preparing the phosphoromorpholidate and of displacing the morpholine by the tetra-tri-n-butylammonium salt of pyrophosphoric acid (J. G. Moffat and H. G. Khorana, J.A.C.S., 1961, 83: 649–658), a second of treating compound (13) with carbonyldiimidazole, then of displacing the imidazole by the same salt of pyrophosphoric acid (Y. Tor and P. D. Dervan, J.A.C.S., 1993, 115, 4461–4467; R. Tipson and B. Townsend, Nucleic Acid Chemistry, part 4 (Wiley-Interscience Publication, New York) 1991, 337–340).

We chose this second method because of the basic conditions and high temperature required by the first are likely to hydrolyse the aliphatic chain placed at 3'. This step was carried out on a small scale and on the unpurified phosphomonoester (compound 13) since we knew that the isolation of compound (14) would necessitate a purification by HPLC.

Another particularly advantageous mode of protection is represented by the synthesis of the triphosphate analogues of 2'-deoxycytidine; the advantage of this method lies in the fact that the four hydrogenolysable groups of compound (19) can be removed in a single step which is step (e).

Synthesis of the triphosphate analogues of 2'-deoxycytidine:

Starting from dC we protected the aromatic amine bore by the base with the aid of 1-(benzyloxycarbonyl) 3-ethylimidazolium tetrafluoroborate according to the conditions of Rappoport et al. (B. E. Watkins, J. S. Kiely and H. Rappoport, J.A.C.S., 1982, 104, 5702–5708) and the 5' primary alcohol function by means of dimethoxyritylation (M. J. Gait, Oligonucleotides synthesis a practical approach (IRL Press at Oxford University Press), 1984, 27–34 and 51; H. Schaller, G. Weimann, B. Lerch and H. G. Khorana, J.A.C.S., 1963, 85, 3821–3827) (compound 16; FIG. 11).

We then introduced the aliphatic chain by the action of the anhydride (6') on compound (16) (D. H. Rammler and H. G. Khorana, J.A.C.S. 1963 85, 1997–2002). This synthesis of compound (17) has also been achieved by "direct" acylation of compound (16) by compound (6) in the presence of 1,8-dicyclohexyl-carbodiimide (DCCI) under stoichiometric conditions and in an equivalent yield (85%).

After deprotection of the 5' primary hydroxyl function of compound (17), carried out in acidic medium as described (M. J. Gait, Oligonucleotides synthesis a practical approach (IRL Press at Oxford University Press), 1984, 27–34 and 51; H. Schaller, G. Weimann, B. Lerch and H. G Khorana, J.A.C.S., 1963, 85, 3821–3827), we phosphorylated compound (18) by the action of dibenzyl phosphorochloridate (P. T. Gilham and H. G. Khorana, J.A.C.S. 1958, 80, 6212–6222) (compound B; FIG. 9). This quite limiting step (48%) has enabled us to obtain the expected compound (19). Its deprotection by hydrogenolysis (P. T. Gilham and H. G. Khorana, J.A.C.S. 1958, 80, 6212–6222; B. E. Watkins, J. S. Kiely and H. Rappoport, J.A.C.S., 1982, 104, 5702–5708; J. H. Rigby, T. L. Moore and S. Rege, J.O.C. 1986, 51, 2400–2402) was carried out under conditions identical with those used for the thymidine analogue and in high yield (78%).

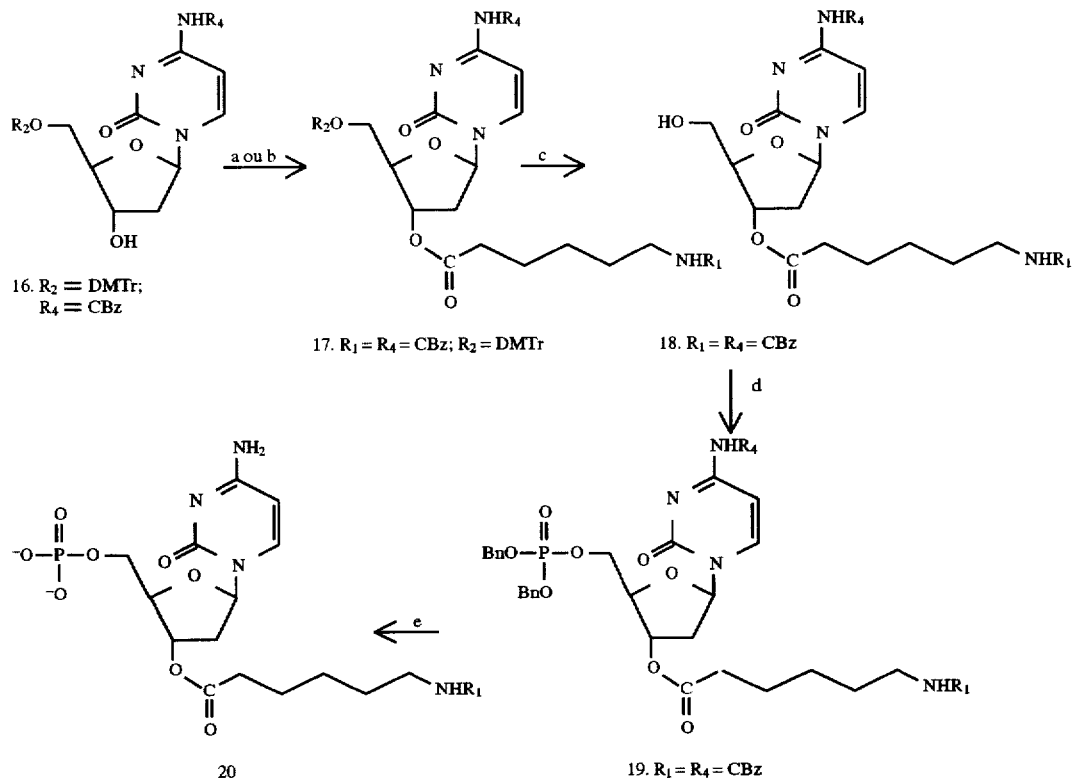

(a): 6; DCCI; DMAP; CH$_3$CN; 25° C.
(b): 6'; DMAP; CH$_3$CN; 25° C.
(c): 2% PhSO$_3$H; CH$_2$Cl$_2$ 70/MeOH 30
(d): B; pyridine N$_2$; −20° C.
(e): Pd/BaSO$_4$; H$_2$; 90% EtOH In a first step we then chose as label for 2'-deoxycytidine (dC), N-methylisatoic acid (FIG. 13) for several reasons:
- the action of N-methylisatoic anhydride does not affect the aromatic amine borne by the pyrimidine base of dC (B. Canard and R. S. Sarfati, 1994 (Gene, in press);
- this label, exited at λ$_{max}$=338 nm, emits at a wavelength, λ$_{max}$=416.5 nm, distinct from that of fluorescein (λ$_{max}$ of emission=519 nm);
- the synthesis of compound (21) would allow us to quickly confirm whether our strategy to obtain the triphosphate from the monophosphate labelled at 3' by the intermediary of the aliphatic chain (compound 6) was a good one.

Starting from compound (21) synthesized under the same experimental conditions as for the thymidine analogue with 5-isothiocyanate-fluorescein (F. S. Wusteman and P. Gacesa Carbohydrates Research, 1993, 241: 237–244), we prepared the triphosphate by successive treatment of compound (21) with carbonyldiimidazole and with pyrophosphoric acid tetra-tri-n-butylammonium salt (Y. Tor and P. D. Dervan, J.A.C.S., 1993, 115: 4461–4467; R. Tipson and B. Townsend, Nucleic Acid Chemistry, part 4 (Wiley-Interscience Publication, New York) 1991, 337–340). The compound (22) thus obtained was purified by chromatography and characterized by phosphorus nuclear magnetic resonance.

These good results prompted us also to label compound (20) with rhodamine (INTERBIOtech, Molecular Probes; "1992-1994 Handbook of fluorescent probes and research chemicals" 1992, 20–41). In fact, this latter fluoresces much more strongly than N-methylisatoic acid and at a wavelength always distinct from that of fluorescein, λmax of emission= 596 nm.

On account of the low solubility of compound (23) only a fraction was purified by HPLC for characterization.

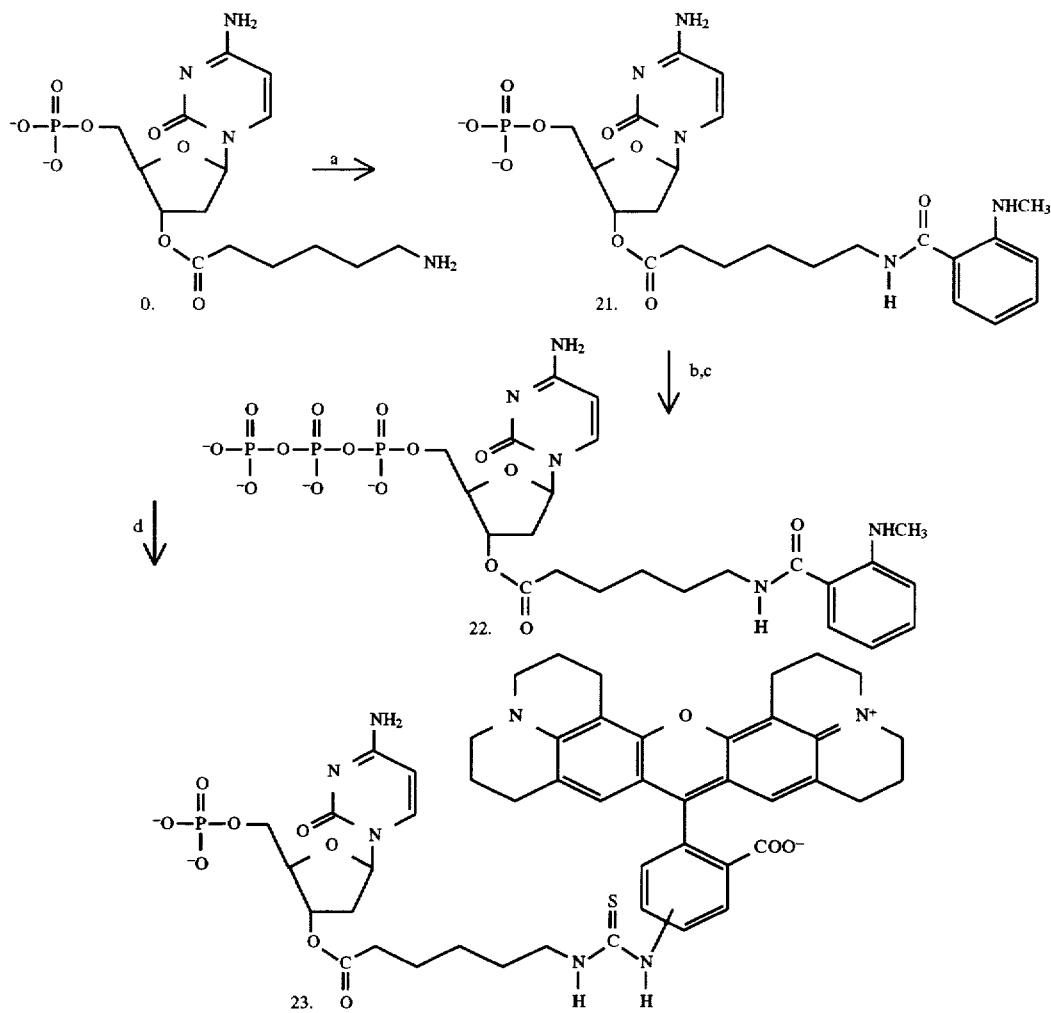

Figure 3:
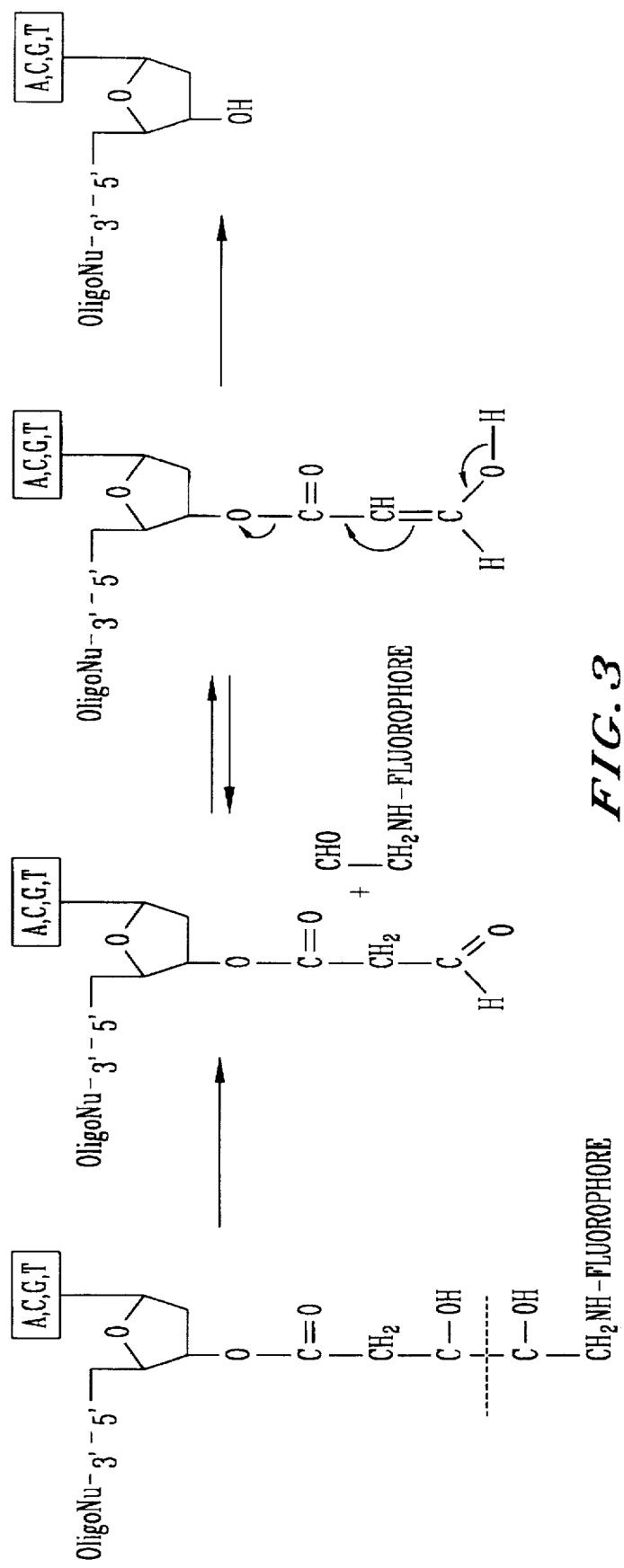
FIG. 3 shows the formula of the derivatives esterified at 3' by 5-amino-2,5-dideoxy D-ribonic acid substituted on the amine function by four different fluorophores, and the method of restoration of the 3' OH function of the sugar by periodate action, followed by β-elimination after enolization.

(a) N-methylisatoic anhydride; pyridine/water; 25° C.
(b) carbonyldiimidazole; DMF; 25° C.
(c) $P_2O_7^{-4}$ $(Bu_3N^+H)_4$; DMF; 25° C.
(d) rhodamine isothiocyanate chloride; pyridine/water; $NaHCO_3$; 25° C.

c) 5-Amino-2,5-dideoxy-D-ribonic acid esters:

The scheme in FIG. 3 indicates how the deprotection and regeneration of the hydroxyl group are carried out: the vicinal diol is oxidized with periodate, this oxidation leading an the one hand, to an aldehyde substituted by the fluorophore whose fluorescence absorption and emission can be measured by the methods described above and, on the other, to an oligonucleotide substituted by an aldehyde which, after enolization, is removed by β-elimination thus releasing the 3' hydroxyl.

The use of oxidation by periodate is compatible with further elongation without re-hybridization of the primer since these conditions do not denature the double stranded DNA corresponding to the primer hybridized to the matrix to be sequenced.

All of the operations may thus be reiterated until the sequence of interest has been sequenced entirely.

The scheme shown in FIG. 9 illustrates clearly the advantages of this type of compound; in fact, in oligonucleotide synthesis the sugars are often temporarily protected in the form of esters of levulinic acid, the levulinates (J. H. Van Boom et al., Tetrahedron Lett. 4875 (1976)). Among other properties of these esters, the deprotection of the alcohols is quantitative within 1 minute at neutral pH and room temperature. Under these conditions the oligonucleotides are stable.

The nucleotides acylated at 3' by 6-amino-2,3,6-trideoxy-D-gluconic acid and oxidized by periodate quantitatively release the fluorochrome and an ester which differs from the levulinic ester only in the replacement of a methyl by a hydrogen (a ketone by an aldehyde).

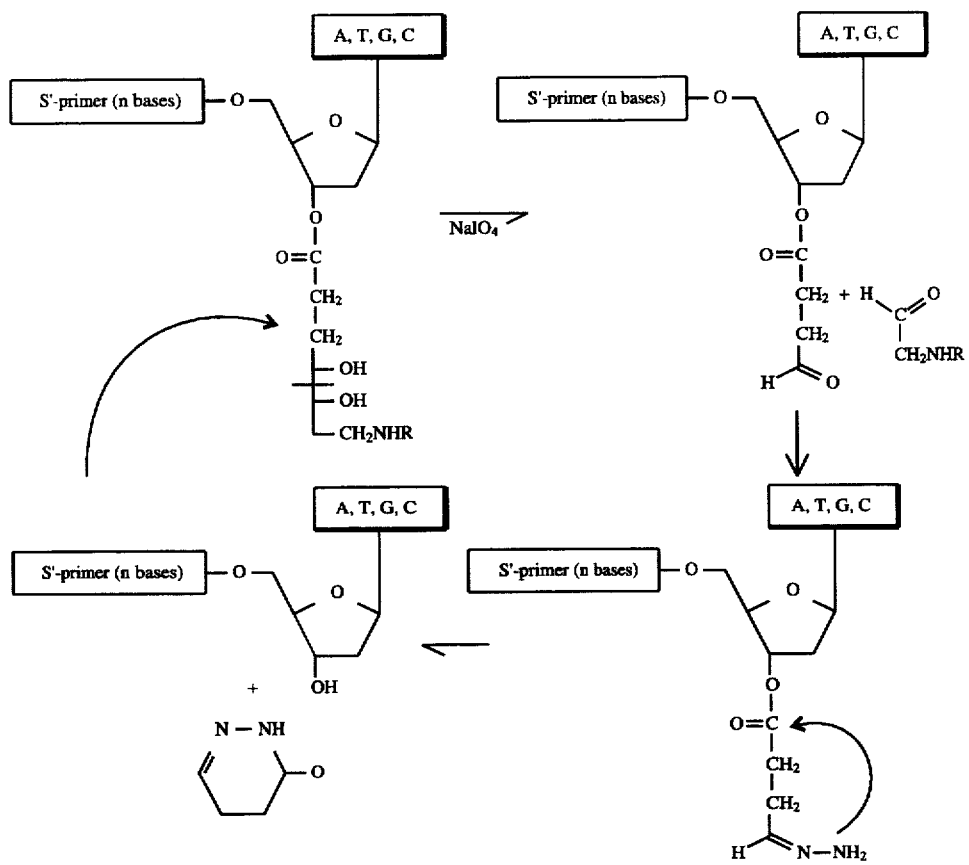

The alcohols are regenerated by the following mechanism in a hydrazine-pyridine-acetic acid-water mixture at neutral pH the ketone function is converted into a hydrazone, the lone electron pair on the nitrogen attacks the carbonyl and the alcohol is released.

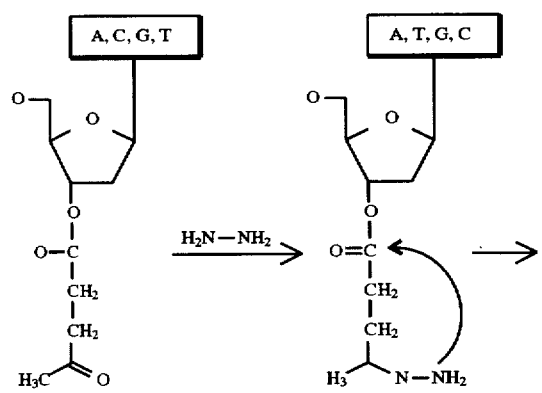

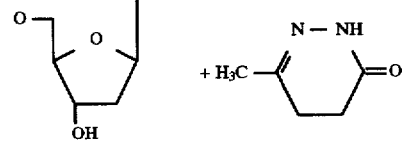

The hydrazones are formed more easily from aldehydes than from ketones, the restoration of the 3'-OH ought thus to be more rapid from an aldehyde.

This type of compound thus exhibits many advantages: they can be rapidly deprotected at room temperature at neutral pH and above all quantitatively.

Example of nuleoctide sequencing along the rpoB gene of a rifampicin-resistant strain of *Mycobacterium leprae*:

The demonstration that the procedure described above can be used to identify the nuleoctide sequences in a complex mixture of single-stranded nucleic acids in a tube or on a column, this method avoids the electrophoresis step on polyacrylamide gel is illustrated by the example below.

1) DNA sample and sequencing target:

In this example, the nuleoctide sequence destined to be analyzed is a part of the gene for the β-subunit of the RNA polymerase of *Mycobacterium leprae* (rpoB).

A change of an amino acid for the codon 425 in the gene confers on the bacterium resistance to rifampicin. Mutations at positions 1, 2 or 3 in the wild-type codon have already been described which replace a serine by a leucine, a phenylalanine or methionine {Honoré N and Cole S. T. (1993), Antimicrobiol. Agents and Chemotherapy 37, No. 3, pp. 414–418}.

The biological starting material is obtained as described in the reference mentioned above; in brief, *M leprae* resistant to rifampicin are extracted from the foot pad of mice and are lysed by a freezing/boiling technique and the samples subjected to amplification by PCR using the primers 1 and 2 specific for the rpoB gene. The amplification product is then analyzed by electrophoresis on agarose gel and used as a sample of starting DNA in the present example.

2) Oligonucleotide primer:

Primer 1 and the rpoB B22 at the reference above. It is a 5'-biotinylated primer with the following sequence:

5'- CAGGACGTCGAGGCGATCAC- 3'

Primer 2 is chosen from the sequence adjacent to the nuleoctide to be analyzed in codon 425 of the ropB gene.

It is constituted of 21 nucleotides with the following sequence:

5'- CAAACCACCCGGGCCCAGCGC- 3' a sequence which corresponds to the wild-type of the rpoB gene of *M. leprae* downstream from the codon 425.

The primer 3 is the "hairpin" primer described in the text above and in FIG. 7.

Its 5' end is phosphorylated and has the following nuleoctide sequence:

5'- GGGCGGCGGGGCTTTATTTGCCCCGC-CGCCCCAAACCA CCCGGGCCCAGCGC- 3'

These primers were obtained in a purified form from the GENSET Corp company (Paris, France).

3) Preparation of the matrices for sequencing:

Primers 1 and 2 are used exactly as described in the reference above (Honoré et al.) to produce a fragment amplified by PCR utilizable for the sequencing of the codon 425 of an unknown sample of *M. leprae* in a final reaction volume of 100 µl.

An aliquot (10 µl) is analyzed by electrophoresis on agarose gel to verify that the PCR amplification is correct.

100 µl of the PCR amplification product are then absorbed on magnetic beads (M280 Dynabeads, streptavidin, Dynal Corp., Norway) coated with streptavidin and prewashed and the non-biotinylated DNA chains are denatured and removed from their complementary chainwhich remains bound to the beads by using 0.1M NaOH as described by the manufacturer.

After several washes the single-stranded DNA matrix bound to the support is in a purified form without interfering with primers or nucleotides.

4) Ligation of "hairpin" primer No. 3:

The matrix bound to the support is resuspended in a ligation buffer (40 mM Tris pH 7.5, 10 mM $MgCl_2$, 10 mM DTT, 0.5 mM ATP), 5 nm of "hairpin" primer No. 3 are added to the mixture, the tube is heated for 2 minutes at 69° C. and 30 minutes at 37° C.

After the addition of 40 units of T4 DNA ligase (Boehringer Corp., Germany), the mixture is incubated fat 3 h at roan temperature with shaking from time to time.

The product thus bound to the beads is washed several times as described by the manufacturer, the last washing being with TE buffer (10 mM Tris pH 8, 1 mM EDTA) and finally suspended in 120 µl of sterile distilled water.

5) Sequencing reaction:

a) Incorporation of a 3'-RT-dNMP at the 3' OH end of the bound "hair-pin" primer 3 (sequencing matrix)

The sequencing matrix is now extended by the "hair-pin" primer which gives a blocked 3' OH end (see FIG. 7). The following solution (elongation solution) is added to the matrix bound to the beads:

10 µl of a 10 fold concentrated buffer (provided by the manufacturer),

10 µl of glycerol

50 µl of 3' RT-dNTP each at a concentration of 2 mM: 3'-anthraniloyl dATP, 3'-N-methyl-anthraniloyl dGTP, 3'-5-methyl-anthraniloyl dCTP, 3'-6-methyl-anthraniloyl dTTP, 10 µl of Taq polymerase(5 units/µl, Boehringer Corp., Germany).

The tube is incubated at 50° C. for 30 minutes with occasional, gentle shaking and then transferred to a magnetic separator to remove the nucleotides not incorporated: 3 washings with 10 mM of Tris pH 7.5, 1 mM EDTA, 2M NaCl, 0.02% Triton X-100, followed by 2 washings with 0.02% Triton X-100 and 1 washing with sterile distilled water.

b) Deprotection at 3':

The sterile distilled water is removed and 30 µl of 0.1M NaOH are added directly to the beads.

The incubation is then performed at 50° C. for 10 minutes. The sample is then magnetized, the supernatant collected, 30 µl of 0.1M NaOH are again added to the beads which are incubated at 50° C. for 10 minutes, then after a magnetic separation, the second supernatant is mixed with the first prior to spectrofluorometric analysis.

The beads are immediately washed exactly as above after the incorporation step and 120 µl of the bead suspension is now ready for a further extension reaction.

c) Identification of the 3' labelling corresponding to the nucleotide incorporated:

6.6 µl of 0.5M Tris pH 8 are added to the pooled supernatants and the mixture is subjected to a spectrofluorometric analysis as described above using a Perkin-Elmer L50B spectrofluorometer and the corresponding HPLC spectrofluorometric detection cell.

The calibration is carried out using reference solutions containing 0.1M NaOH and 50 mM Tris pH 8.

Individual spectra corresponding to the 4 derivatives lacking anthranilate are measured in the same buffer and their maximal emission is determined.

Then, their excitation spectra are determined as described above.

In this manner, each label is defined by two specific wavelengths, namely the maximum in nanometers for excitation and emission.

After having loaded the sample into the detection cell, the excitation is carried out at 310 nm and the emission spectrum is measured between 340 nm and 500 nm.

The spectrum is corrected for any solvent effect by subtracting the reference spectrum, the curve is smoothed and the wavelengths corresponding to the maximum described above are determined by using a computer program supplied by the manufacturer.

The supernatants subjected to the spectrofluorometric analysis give as result 317 nm and 409 nm for the excitation and emission maxima, respectively.

This identifies unambiguously a dC residue incorporated at the 3' end of the sequencing matrix.

6) Repetition of the procedure: sequencing of the codon 425 of the rpoB gene of *M. leprae* of an isolate resistant to rifampicin:

The 120 µl of bead suspension are now subjected again to steps a), b) and c) of the sequencing reaction in order to identify the next nucleotide of codon 425 of the rifampicin-resistant isolate of *M. leprae*.

In this case, the excitation and emission maxima are 315 nm and 397 nm, respectively and this identifies a dA residue incorporated after the dC of the preceding reaction.

The next complete sequencing cycle (step 5a), b), c)) identifies the excitation and emission wavelengths at 289 nm and 403 nm, respectively, which is typical of a dT residue incorporated at the 3' end of the sequencing matrix.

Thus, from the experiments we conclude that the nucleotide sequence of the codon 425 of the rpoB gene of the sample analyzed is ATG which codes for a methionine in place of a serine, the latter being characteristic of the wild-type phenotype.

Since this sort of mutation has been described in isolates of the rpoB3 type (see Honoré N. et al.), the experiments described above give the molecular bases of rifampicin resistance in the gene of the *M. leprae* isolate.

We claim:

1. An ester of a deoxyribonucleoside or ribonucleoside 5' triphosphate having formula (II):

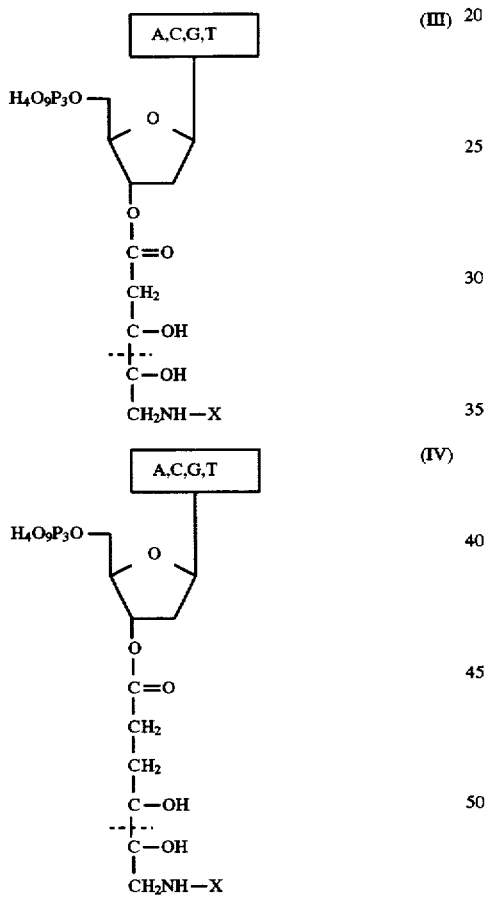

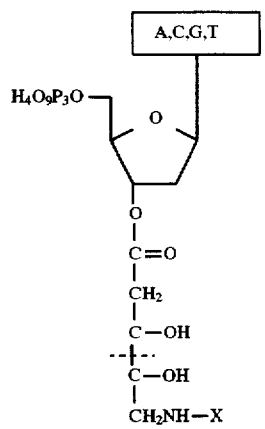

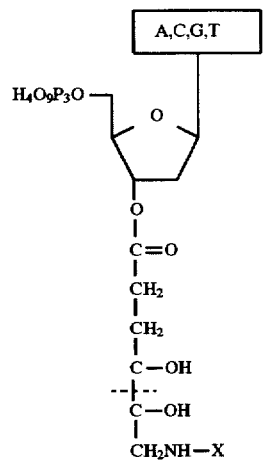

where X is a fluorophore or hydrogen, in which the 3' hydroxyl can be restored by cleavage of the caproic acid when substituted by said fluorophore in basic medium or by action of an enzyme.

2. The ester of claim 1, where X is a fluorophore.

3. An ester of a deoxyribonucleoside or ribonucleoside 5' triphosphate of formula (III) or (IV):

where X is a fluorophore or hydrogen, and in which the 3' hydroxyl group can be liberated in two steps which are:

oxidation of the vicinal diol by periodate; and enolization and β-elimination of the 3' aldehyde when said ester has formula (III), or elimination as a result of the action of hydrazine when said ester has formula (IV).

4. A method of sequencing a polynucleotide chain, comprising the steps of:

(a) constructing a primer;

(b) adding to said primer by a nucleic acid polymerase an ester of a deoxyribonucleoside or ribonucleoside 5' triphosphate of formula (II), (III) or (IV) esterified at the 3' OH such that its incorporation thereof blocks any subsequent elongation and said ester bears a label specific for each of the four bases of said esterified nucleotides;

(c) hydrolyzing the 3' OH function by chemical or enzymatic hydrolysis;

(d) characterizing the hydrozylate formed for a given nucleotide;

(e) repeating steps (a)–(d) in order to characterize the next nucleotide.

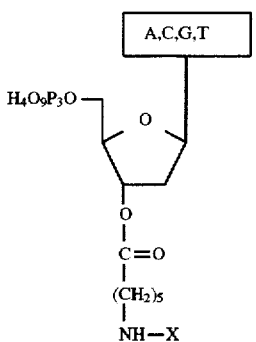

(II)

where X is a fluorophore or hydrogen, in which the 3' hydroxyl can be restored by cleavage of the caproic acid when substituted by said fluorophore in basic medium or by action of an enzyme;

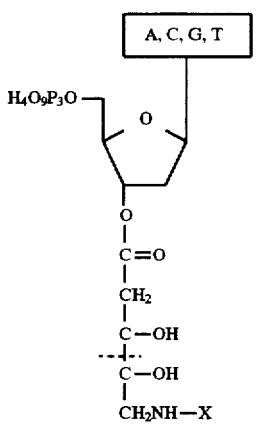

(III)

where X is a fluorophore or hydrogen, and in which the 3' hydroxyl group can be liberated in two steps which are:
oxidation of the vicinal diol by periodate; and
enolization and β-elimination of the 3' aldehyde;

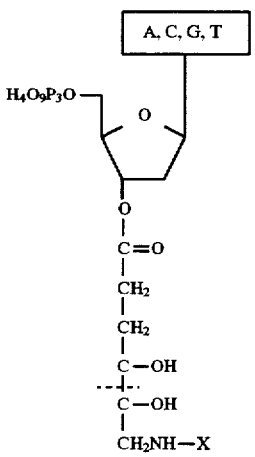

(IV)

where X is a fluorophore or hydrogen, and in which the 3' hydroxyl group can be liberated in two steps which are:
oxidation of the vicinal diol by periodate; and
elimination as a result of the action of hydrazine.

5. The method of claim 4, wherein said primer is a hairpin primer which is phosphorylated at the 5' end, has a part of its 3' sequence identical with that of a primer used in a PCR reaction to produce the DNA matrix to be sequenced, and is compatible with deprotection in basic medium.

6. The method of claim 4, wherein said ester is the bearer of a compound detectable by fluorescence, where the excitation and emission characteristics of said compound being characteristic of each of the four nucleotides.

7. The method of claim 4, wherein said ester has formula (II).

8. The method of claim 4, wherein said ester has formula (III).

9. The method of claim 4, wherein said ester has formula (IV).

10. The method of claim 4, where steps (a)–(e) are repeated to detect point mutations in said polynucleotide chain involving between 2 and 20 nucleotides.

11. The method of claim 4, wherein steps (a)–(e) are repeated to search for a specific sequence in a complex mixture of nucleic acids.

12. The method of claim 4, wherein all four of said esters of a deoxyribonucleoside or ribonucleoside 5' triphosphate of formula (II), (III) or (IV) are used at the same time in step (b) and said nucleic acid polymerase lacks a 3'-5' exonucleolytic activity.

13. The method of claim 13, wherein said nucleic acid polymerase is Taq polymerase.

14. The method of claim 13, wherein all four of said esters have formula (II).

15. The method of claim 13, wherein all four of said esters have formula (III).

16. The method of claim 13, wherein all four of said esters have formula (IV).

17. A kit for the diagnosis of the presence in a sample of nucleic acid sequence, comprising:

(a) a sequencing primer;

(b) four esters of a deoxyribonucleoside or ribonucleoside 5' triphosphate of formula (II), (III) or (IV); and (c) a nucleic acid polymerase which lacks a 3'-5' exonucleolytic activity; and (d) optionally, a solid phase to immobilize the nucleic acid to be analyzed or said primer.

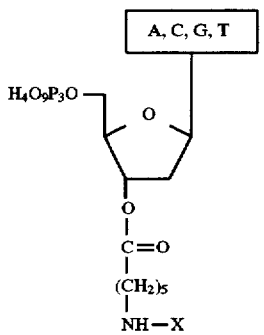

(II)

where X is a fluorophore or hydrogen, in which the 3' hydroxyl can be restored by cleavage of the caproic acid when substituted by said fluorophore in basic medium or by action of an enzyme;

27

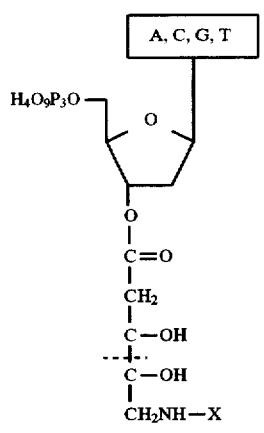

(III)

where X is a fluorophore or hydrogen, and in which the 3' hydroxyl group can be liberated in two steps which are:

oxidation of the vicinal diol by periodate; and enolization and β-elimination of the 3' aldehyde;

28

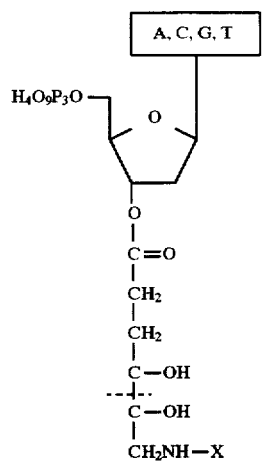

(IV)

where X is a fluorophore or hydrogen, and in which the 3' hydroxyl group can be liberated in two steps which are:
oxidation of the vicinal diol by periodate; and
elimination as a result of the action of hydrazine.

18. The kit of claim 17, wherein said nucleic acid polymerase is Taq DNA polymerase.

19. The kit of claim 17, which contains said solid phase.

* * * * *